United States Patent
Arnett et al.

(10) Patent No.: US 6,908,555 B2
(45) Date of Patent: Jun. 21, 2005

(54) BIOSOLIDS FLOW-THROUGH THERMOPHILIC TREATMENT PROCESS

(75) Inventors: Clifford J. Arnett, Columbus, GA (US); Joseph B. Farrell, Cincinnati, OH (US); Daniel T. Hull, III, Atlanta, GA (US); Steven J. Krugel, Seattle, WA (US); Perry L. Schafer, Sacramento, CA (US); Billy G. Turner, Columbus, GA (US); Warren R. Uhte, Fort Jones, CA (US); John L. Willis, Norcross, GA (US)

(73) Assignee: Columbus Water Works, Columbus, GA (US)

( * ) Notice: Subject to any disclaimer, the term of this patent is extended or adjusted under 35 U.S.C. 154(b) by 22 days.

(21) Appl. No.: 10/425,131

(22) Filed: Apr. 28, 2003

(65) Prior Publication Data

US 2004/0011718 A1 Jan. 22, 2004

Related U.S. Application Data

(60) Provisional application No. 60/376,726, filed on Apr. 29, 2002.

(51) Int. Cl.[7] .............................. C02F 3/28; C02F 11/04
(52) U.S. Cl. ........................ 210/603; 210/613; 210/181; 210/259
(58) Field of Search ................................ 210/603, 612, 210/613, 252, 259, 175, 181, 908

(56) References Cited

U.S. PATENT DOCUMENTS

| | | | | |
|---|---|---|---|---|
| 4,396,402 A | * | 8/1983 | Ghosh ....................... | 48/197 A |
| 5,746,919 A | * | 5/1998 | Dague et al. ............... | 210/603 |
| 5,954,964 A | * | 9/1999 | Nielsen et al. .............. | 210/609 |
| 6,047,768 A | * | 4/2000 | Buehler, III ................ | 165/143 |
| 6,521,133 B1 | * | 2/2003 | Roediger .................... | 210/742 |

FOREIGN PATENT DOCUMENTS

DE 3248703 A1 * 7/1984

OTHER PUBLICATIONS

William F. Garber et al.; *Thermophillic Digestion at the Hyperion Treatment Plant*; Journal WPCF, vol. 47, No. 5, pp950–961, 1975.

Gerald L. Hernandez et al., *Hyperion Advanced Digestion Pilot Program*; 16th Annual Residuals and Biosolids Management Conference; WERF 2002.

John L. Willis et al., *Operational Improvements from Start–up of OWASA'S Class–A Thermophillic Anaerobic Digestion System*; WEFTEC 2001; WERF 2001.

* cited by examiner

*Primary Examiner*—Fred G. Prince
(74) *Attorney, Agent, or Firm*—Robert D. Varitz, P. C.

(57) ABSTRACT

A method of treating wastewater sludge includes pumping, continuously, raw sludge into a first digester and treating the raw sludge at a specific temperature of between about 51° C. to 60° C.; transferring the treated wastewater sludge to a batch tank; treating the wastewater sludge in the batch tank, anaerobically, at a thermophilic temperature which is not more than 2° C. warmer than the specific temperature in the first digester; and disposing of the treated wastewater sludge as a Class A biosolid. A wastewater sludge treatment system includes a first thermophilic digester for treating raw wastewater sludge at a specific temperature in a range of between about 51° C. to 60° C., and discharging a treated wastewater sludge; a batch tank for receiving the treated wastewater sludge discharged from the first digester and for thermophilically treating sludge at a temperature in a range of between about 51° C. to 60° C. and not more than 2° C. warmer than the specific temperature in the first digester, for between about 0.5 hours and 5 hours; and a disposal mechanism for disposing of the treated wastewater sludge as a Class A biosolid.

18 Claims, 6 Drawing Sheets

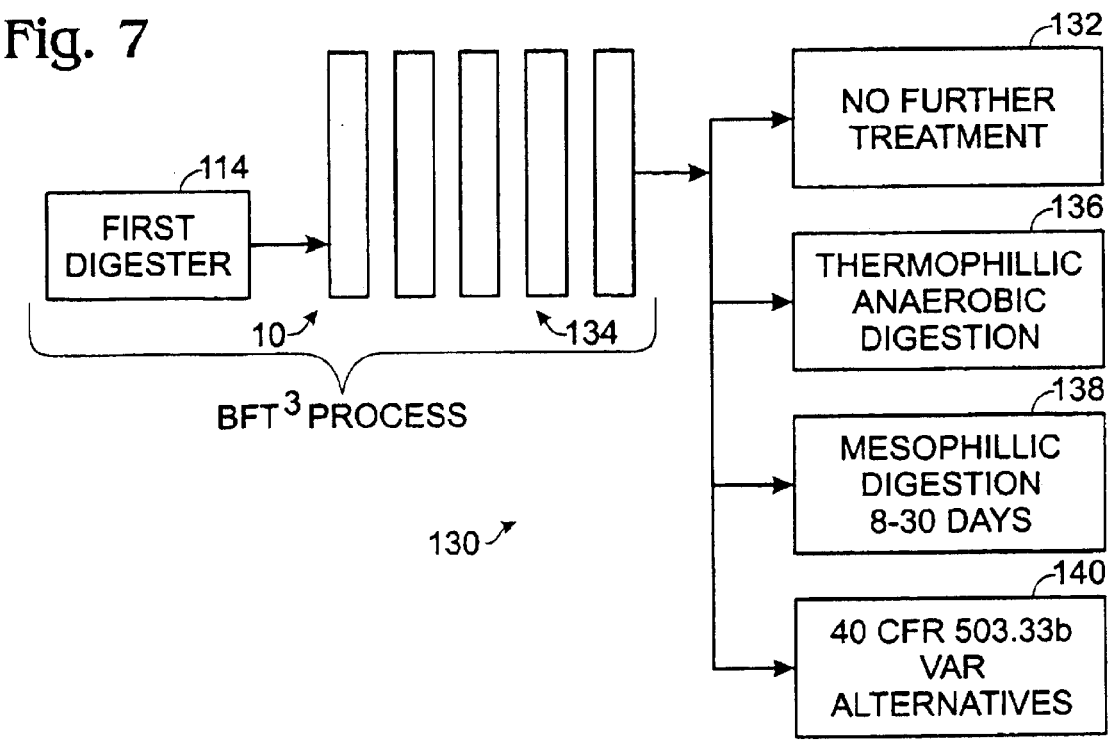
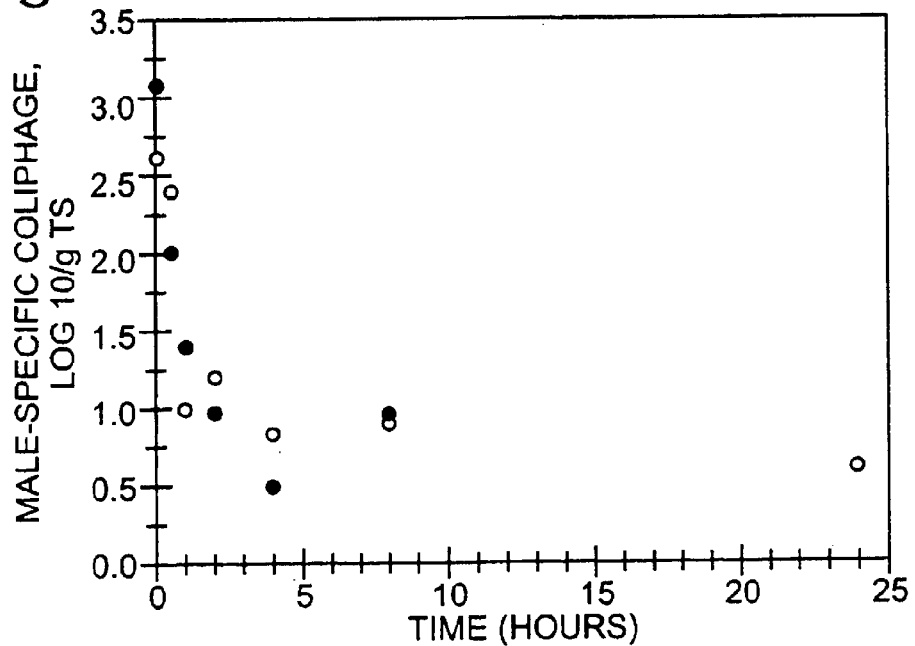

US 6,908,555 B2

BIOSOLIDS FLOW-THROUGH THERMOPHILIC TREATMENT PROCESS

This application claims benefit under 35 U.S.C. 119(e) to U.S. Provisional Application Ser. No. 60/376,726, filed Apr. 29, 2002.

FIELD OF THE INVENTION

This invention relates to wastewater treatment, and specifically to a method of treating wastewater sludge using a thermophilic treatment process.

BACKGROUND OF THE INVENTION

Land application of treated wastewater sludge, or biosolids, is controversial because the material therein contains human pathogens. Wastewater treatment agency managers are concerned about the future of biosolids land applications in their states. The United States Environmental Protection Agency's (EPA's) Class A pathogen standards require the virtual elimination of pathogens in biosolids. In accordance with 40 CFR § 503.32 (a)(5), Class A—Alternative 3 and 40 CFR § 503.32(a)(6)—Alternative 4, EPA Class A pathogen requirements are met in biosolids when fecal coliform densities are less than 1,000 most probable number (MPN) per gram total solids; or when *Salmonella* densities are less than 3 MPN per four grams total solids. Enteric virus density must be less than one plaque-forming unit per four grams of total solids, and helminth ova is less than one viable helminth ova per four grams of total solids. Additionally, EPA provides time and temperature requirements under 40 CFR § 503.32(a)(3—Alternative 1, that state the required reduction in pathogen densities.

Meeting Class A standards will significantly increase the opportunity for biosolids recycling, however, known processes which achieve Class A pathogen densities in biosolids are generally costly, and in some instances, cost prohibitive. The provision of a low-cost method of biosolids treatment, which will meet Class A standards will offer an additional biosolids management option. Known thermophilic anaerobic digestion processes are not classified as a Process to Further Reduce Pathogens (PFRP) under 40 CFR Part 503.

In Class A sludge land application, three main criteria need to be met:

1) Pathogen Kill. This is accomplished by the BFT3 process of the invention;

2) Vector Attraction Reduction (VAR). This refers to the degree that the finished Biosolids (treated sludge) have been stabilized. Unstable solids will attract flies and other vectors as well as creating nuisance odors. This criterion must be met equally by both Class A and Class B materials. A major regulated criterion is that at least 38% of the volatile solids must be destroyed in anaerobic digestion. This can be reliably accomplished by holding sludge in an anaerobic digester for certain mean detention times, depending on the process used. For example, most mesophilic-only anaerobic systems operate in the 35° C. range and typically are designed for 20-day mean cell residence time (MCRT), and could possibly still meet the criteria in as little as 12 to 15 days. A thermophilic-only system might be designed for a 15-day MCRT and could possibly meet the criterion as little as 7 to 10 days. Temperature-phased systems, e.g., thermophilic treatment followed by mesophilic treatment, have been designed for as little as 12 days total MCRT.

3) Pollutants. This criterion refers to the concentrations of certain regulated pollutants and metals in the finished biosolids. This is usually a function of the industries that discharge to a wastewater system more so than any process used in treating the wastewater sludge.

Anaerobic digestion has been one of the most widely used processes for the stabilization of primary and secondary sludges produced at municipal wastewater treatment facilities. The majority of applications of anaerobic digestion to wastewater sludges have been in the mesophilic temperature range, from 35° C. to 40° C. (95° F. to 104° F.). Anaerobic sludge digestion in the thermophilic temperature range from 45° C. to 65° C. (113° F. to 149° F.) has been practiced to only a limited extent.

The limited use of anaerobic digestion at temperatures above the mesophilic range is due to higher energy requirements to obtain the higher thermophilic temperature, and because early reviews of such systems in the relevant literature identified problems, such as poor process stability, increased odor, and lower quality supernatant (filtrate/centrate). Many of these concerns have been proven to be untrue in currently-operating thermophilic systems. The advantages of thermophilic anaerobic digestion over mesophilic anaerobic digestion include increased stabilization and methane production rates, and improved sludge dewatering properties. Since the advent of the 40 CFR Part 503 Regulations, more studies have focused on the destruction of pathogenic organisms.

Thermophilic anaerobic digestion has an advantage of improving pathogen destruction, and has the potential to meet the pathogen quality requirements of EPA's Class A biosolids. The EPA Pathogenic Equivalency Committee (PEC) has stated that 2-$\log_{10}$ and 3-$\log_{10}$ reduction in pathogenic density of *Ascaris* ova and poliovirus, respectively, will be required in order to prove Class-A performance.

Research has shown that pathogen destruction in municipal sludge digestion follows a time/temperature relationship, wherein higher temperatures require shorter exposure times for pathogen destruction. Data have been collected demonstrating survival rates of various pathogens in municipal sludge digestion. These data suggest that thermophilic digestion achieves pathogenic bacteria reduction rates well in excess of two orders of magnitude higher than mesophilic digestion, and may meet the pathogen densities required for Class A sludge.

Anaerobic digestion has been performed in cylindrical or egg-shaped vessels for many years. However, the physical requirements for a pipeline, or plug-flow, digester, or reactor, are, as yet, unproven. While the 40 CFR, Part 503 regulation allows for use of plug-flow reactors to meet time and temperature requirements, the particulars of such a system are currently undefined. While standards are not currently defined for a thermophilic treatment process in a plug-flow reactor, one may be designed based on application of engineering and science.

SUMMARY OF THE INVENTION

The Biosolids Flow-Through Thermophilic Treatment (BFT³) process, as developed by the inventors hereof for Columbus Water Works of Columbus, Ga., and referred to herein as the Columbus Biosolids Flow-Through Thermophilic Treatment (CBFT³) process, is a two-stage process consisting of a complete-mix, thermophilic anaerobic digester, with continuous or intermittent feed and withdrawal, followed by a thermophilic anaerobic batch detention vessel. The complete-mix digester (the first stage) is defined for a worst-case continuous feed and simultaneous continuous withdrawal operation. Any less-than-continuous operation of the first stage may be expected to improve pathogen destruction and will still provide Class-A treatment. The thermophilic, anaerobic batch detention vessel (the second process stage) may either be a dedicated batch tank(s), or may alternatively be a plug-flow reactor designed to insure that all particles of sludge are subjected to the required batch time and temperature over the entire range of possible flow rates.

A method of treating wastewater sludge includes pumping, continuously, raw sludge into a first digester and treating the raw sludge at a specific temperature of between about 51° C. to 60° C.; transferring the treated wastewater sludge to a batch tank; treating the wastewater sludge in the batch tank, anaerobically, at a thermophilic temperature which is not more than 2° C. warmer than the specific temperature in the first digester; and disposing of the treated wastewater sludge as a Class A biosolid.

A wastewater sludge treatment system includes a first thermophilic digester for treating raw wastewater sludge at a specific temperature in a range of between about 51° C. to 60° C., and discharging a treated wastewater sludge; a batch tank for receiving the treated wastewater sludge discharged from the first digester and for thermophilically treating sludge at a temperature in a range of between about 51° C. to 60° C. and not more than 2° C. warmer than the specific temperature in the first digester, for between about 0.5 hours and 5 hours; and a disposal mechanism for disposing of the treated wastewater sludge as a Class A biosolid.

This summary and objectives of the invention are provided to enable quick comprehension of the nature of the invention. A more thorough understanding of the invention may be obtained by reference to the following detailed description of the preferred embodiment of the invention in connection with the drawings.

BRIEF DESCRIPTION OF THE DRAWINGS

FIG. 7 is a block diagram of a system incorporating various embodiments of the method of the invention to achieve VAR.

FIG. 10 is a plot of male-specific coliphage data from 53° C. spiked-batch tests.

DETAILED DESCRIPTION OF THE PREFERRED EMBODIMENT

Figure 1:
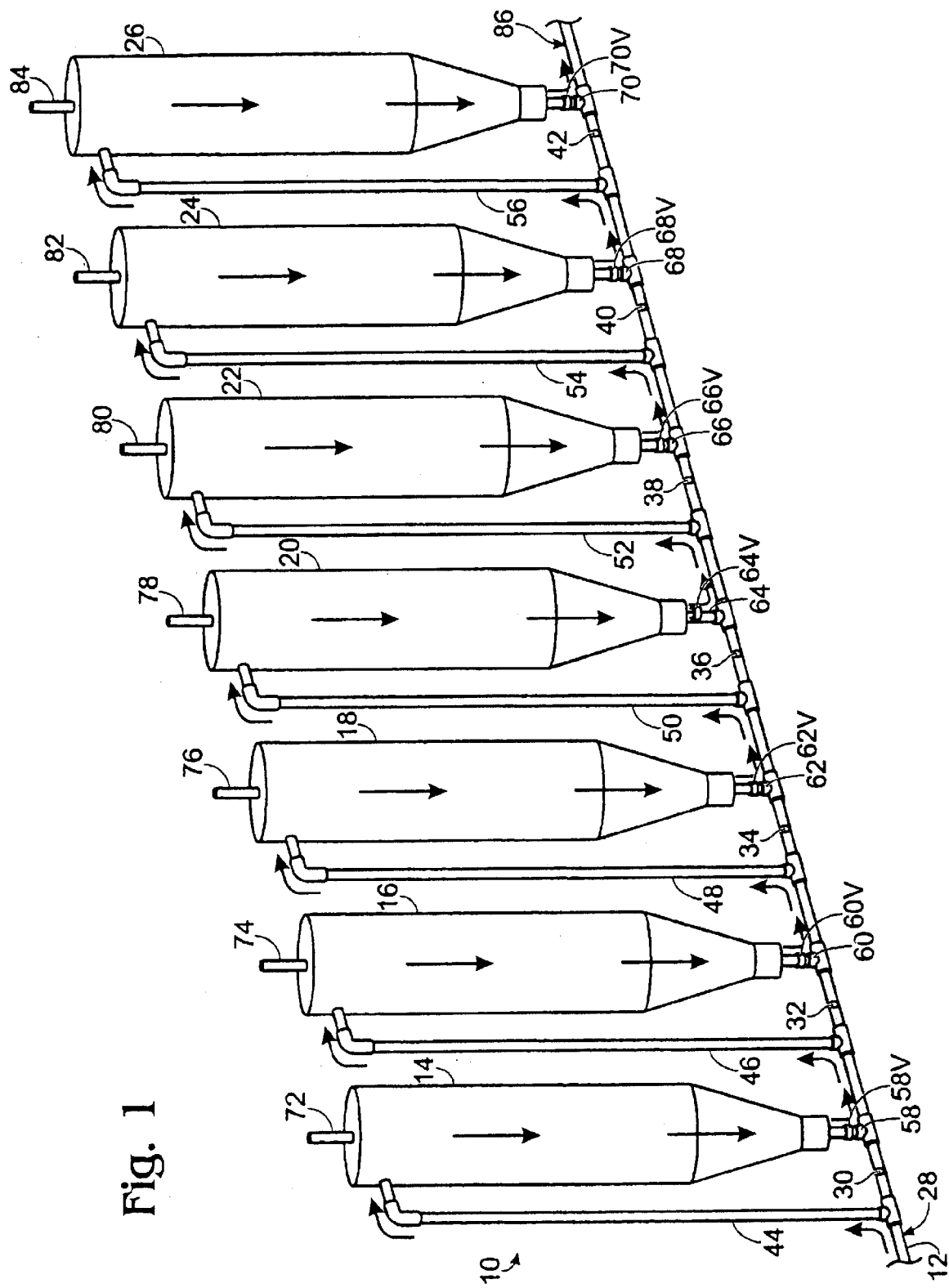
FIG. 1 is a schematic representation of a plug-flow reactor of the invention.

The inventors hereof have developed an approach to achieving the Class A criteria with thermophilic anaerobic digestion called Biosolids Flow-Through Thermophilic Treatment ($BFT^3$). The $BFT^3$ process combines a complete-mix, continuous-flow reactor (the first reactor or digester) followed by a dedicated batch reactor (the second reactor or digester) for a batch detention step that is much shorter than that required by the Environmental Protection Agency (EPA), as stated in 40 CFR § 503.32(a)(3)—Alternative 1, for solid content less than 7%. The batch detention step can also be achieved using a nominally plug-flow reactor, to digest sludge while encouraging sludge movement in a plug-flow manner. In either case, the second reactor compensates for any short-circuiting that might occur in the mixed, continuous-flow reactor. National Class A equivalency is being sought for the $BFT^3$ process through a demonstration project. The demonstration project includes a laboratory investigation, full-scale prototype evaluation of the plug-flow reactor, and a full-scale demonstration at the South Columbus (Georgia, USA) Water Resource Facility (SCWRF).

The $BFT^3$ method of the invention is a process to effectively reduce pathogen densities in sludge to meet Class-A requirements as defined in 40 CFR, Part 503, and to meet expected standards as may be defined by the Environmental Protection Agency (EPA) Pathogenic Equivalency Committee (PEC).

$BFT^3$ provides critical design information for utilities to cost-effectively upgrade to Class A biosolids treatment. The method and system of the invention provide reactor configuration, hydraulics, and pathogen destruction allowing Class A biosolids production using a cost-effective, easy-to-operate, flow-through system.

Process Definition

The current $CBFT^3$ process definition is as follows: A complete-mix, continuous-feed stirred tank reactor (CFSTR) operated at a specific temperature in a range of between about 51° C. to 60° C., followed by a batch detention step of between one half-hour and five hours that is also performed at the same specific temperature, or at a temperature no more than 2° C. greater than the specific temperature. Because the batch detention step is a continuation of the thermophilic digestion process, no more than 2° C. of additional heating may occur between the CFSTR and the batch tank. The batch tank can either be a pure batch operation or an "equivalent batch detention step," such as a plug-flow reactor. In the case of an equivalent batch detention step, the minimum detention time in the equivalent batch vessel must be proven to exceed the one hour required batch time. Operational temperatures may be set from between about 51° C. to 60° C. in the plug-flow reactor of the invention. It should be appreciated that the invention addresses the first of the three Class A criteria, i.e. pathogen kill. The process definition currently does not address VAR, however, this does not mean, for example, that, given a CFSTR with a mean cell residence time (MCRT) of 12 days to 15 days, a pure thermophilic system could not meet this requirement with only the $BFT^3$ elements. Each new system using $BFT^3$ should be evaluated independently to see how the VAR requirement will be satisfied. In one embodiment of the method of the invention, two existing digesters, operating in mesophilic temperature ranges downstream of the $BFT^3$ process are used to further reduce volatile solids, resulting in better VAR and less material to haul offsite. Additionally, the pollutant concentration issue is currently not addressed by the $CBFT^3$ process.

Basis of Process Definition

Laboratory-scale testing was conducted under contract at the University of North Carolina, Chapel Hill (UNC), to determine the effectiveness of pathogen destruction of the process defined herein at laboratory scale. All of the testing results presented herein were collected using co-thickened waste activated and primary sludges from the South Columbus Water Resource Facility (SCWRF) as the process feed stock. Four series of tests were conducted, and the results presented later herein. These tests included: (1) Testing of the BFT$^3$ process at 55° C.; (2) Spiked-batch pathogen destruction at 55° C.; (3) Testing of the BFT$^3$ process at 53° C.; and (4) Spiked-batch pathogen destruction at 53° C.

Prior to this testing, the EPA Pathogenic Equivalency Committee (PEC) identified that 2-$\log_{10}$ and 3-$\log_{10}$ pathogen density reduction of Ascaris ova and poliovirus, respectively would be required in order to prove Class-A performance. The CBFT$^3$ process tests at both 55° C. and 53° C. demonstrated that *Ascaris* ova and poliovirus were inactivated by greater than 2-$\log_{10}$ and 3-$\log_{10}$ density reduction, respectively by the CFSTR. In addition, no viable *Ascaris* ova or poliovirus were detected in the effluent from the CFSTR at either temperature in any of the CBFT$^3$ process tests.

The spiked-batch tests were done in order to "quantify" the effectiveness of the batch holding time downstream of the CFSTRs because the lack of any pathogens in the CFSTR effluent precluded the measurement of any further destruction. The spiked-batch tests took CFSTR effluent and inoculated the feed to a batch reactor with *Ascaris* ova and poliovirus so that the pathogen destruction could be observed. As expected, the tests at 53° C. required longer batch times than the spiked-batch tests at 55° C. to reach the desired $\log_{10}$ reductions and eventually, 4 complete inactivation.

All of the laboratory-scale work has been conducted to minimize the likelihood of an anti-microbial agent other than temperature contributing to the observed pathogen inactivation. The feedstock concentration has consistently been less than 3.5% total solids, and often closer to 3.0% total solids. This is considerably lower than found in most thermophilic digesters, where feed stocks range from 5.0% to 6.5% total solids. The lower solids concentration results in lower concentrations of ammonia and volatile acids constituents which may improve pathogen inactivation. In the laboratory-scale work, no known antimicrobial agents have been detected in either the raw feedstock or the digesting mass.

Plug-Flow Reactor Configuration

Figure 2:
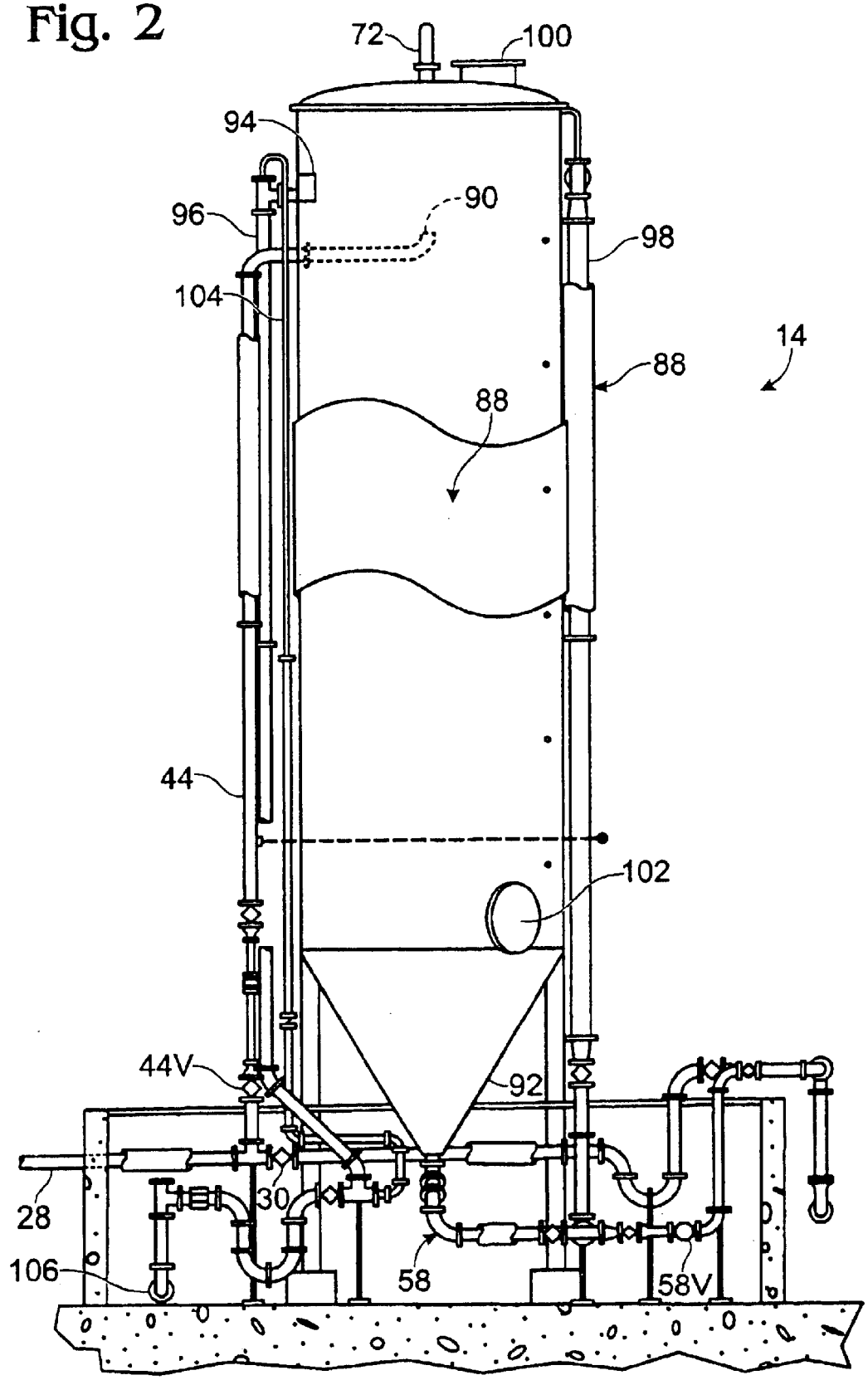
FIG. 2 is a cross-section of a single reactor vessel of the invention.

The BFT$^3$ method of the invention, as used in the CBFT$^3$ embodiment, includes a complete-mix, continuous-feed thermophilic anaerobic digester, followed by a series of tall reactors, e.g., plug-flow reactors, insulated and sized to provide the required detention time at the identified designed temperature range. A schematic representation of the batch tank, plug-flow reactor of the invention is provided in FIG. 1, generally at 10. Sludge, from a thermophilic-digesting system (the first digester or reactor) enters the plug-flow reactor, the second digester or reactor, also referred to herein as the batch tank(s), at 12. Plug-flow reactor 10 includes a number of vertically disposed plug-flow reactor vessels, 14, 16, 18, 20, 22, 24 and 26. Although seven reactor vessels are depicted in FIG. 1, any number of reactor vessels may be used, so long as the identified minimum detention time is achieved. Each reactor vessel is essentially a large diameter pipe, which will provide for retention of biosolids (wastewater sludge) for a pre-determined period of time in order to thermophilically treat the biosolids. The reactor vessels may be cylindrical or rectangular, having a conical-shaped bottom feeding into an outflow pipe. FIG. 2 depicts the details of a single reactor vessel 14 of the invention. In the preferred embodiment of the plug flow reactor, each reactor vessel is approximately ten feet in diameter, stands about forty-two feet high, and has an eight-foot high cone at the base thereof. In other embodiments of the invention, the vessels may be six-foot cylindrical pipes having a length of about thirty feet, or, in another embodiment, the vessels may have a four-foot square cross section, and be about thirty feet tall.

A sludge feed manifold 28 extends along the length of plug-flow reactor 10, and, at the location of each vessel, includes a by-pass valve, 30, 32, 34, 36, 38, 40 and 42, respectively. Each vessel communicates with manifold 28 through an inflow small-diameter sludge feed pipe, 44, 46, 48, 50, 52, 54 and 56, respectively, which includes a valve, e.g., 44V, 46V, etc., therein. A small diameter pipe is used to pass biosolids to the top of the vessels to prevent settling of solids in the biosolids. Treated biosolids exits the vessels through an outflow small diameter pipe, 58, 60, 62, 64, 66, 68 and 70, also containing a valve, e.g., 58V, 60V, etc. Gas vents, 72, 74, 76, 78, 80, 82 and 84, respectively, are provided on each vessel.

The valves on the inflow and outflow pipes, and the valves in manifold 28, allow the specific routing of biosolids to and from a particular reactor vessel. Biosolids may be routed through all of the vessels in the plug-flow reactor, or directed through less than all of the vessels, depending on the flow rate, the occurrences of maintenance on any part of the plug-flow reactor, and the desired retention time for this part of the treatment process. Once wastewater sludge has been fully treated, it exits plug-flow reactor 10 through manifold 28 at 86.

While the BFT$^3$ process description provides for either a dedicated batch operation downstream of the CFSTR or an "equivalent batch", the embodiment of the CBFT$^3$ systems calls for the use of a plug-flow digester as an equivalent batch. Four different baffle arrangements are provided in the reactor vessel, and will be described later herein.

Each plug-flow reactor vessel is designed as a top-feed, downward-flow vessel. The digesting sludge is introduced at thermophilic temperatures, 51° C. to 60° C. The tank and pipes are insulated, 88, so as to reduce heat loss. The inlet to the plug-flow digester is a small diameter, sludge feed pipe 44, having a nozzle 90, directed upwards in the center of the tank. The pipe is sized so that the velocity in the pipe keeps grit in suspension, and is directed upward so that the entrance velocity energy is dissipated in a direction opposite the prevailing velocity gradient in the reactor. As this velocity energy is dissipated, the liquid reflects off the water surface in the reactor and is directed toward the perimeter of the digester so as to better use the entire cross-sectional area as "effective volume."

As the applied sludge continues to digest, it produces digester gas, which is largely composed of methane and carbon dioxide, as volatile solids are consumed by the microbial population. The gas is collected at the top of the digester in a 6-inch low pressure sludge gas (LSG) pipe (72 for reactor vessel 14). Sludge also commonly contains grit that settles on horizontal surfaces and requires higher velocities to be re-suspended. The conical bottom 92 of the plug-flow digester directs settling grit to a smaller diameter pipe (58 for reactor vessel 14) having higher flow velocities which are capable of moving the grit to the next downstream process unit.

Sludge is also likely to contain floatable materials, such as greases and plastics, which are referred to as "scum". As the downward velocity in the plug-flow digester is fairly low, scum is likely to build up at the top of the digester and not progress down toward the conical bottom. Scum can be removed from the plug-flow digester by closing discharge valve 58V and, when the level rises above weir 94, located near the top of the reactor vessel, the floatable material on the surface is removed and returned to the plant headworks through a weir discharge pipe 96. Also included in reactor vessel 14 is a standpipe 98, a two-foot diameter top hatch 100, a side hatch 102, and flush water pipe 104 and flush water manifold 106.

Four general baffle arrangements are described herein:

Configuration A. No baffles (not shown).

Figure 3:
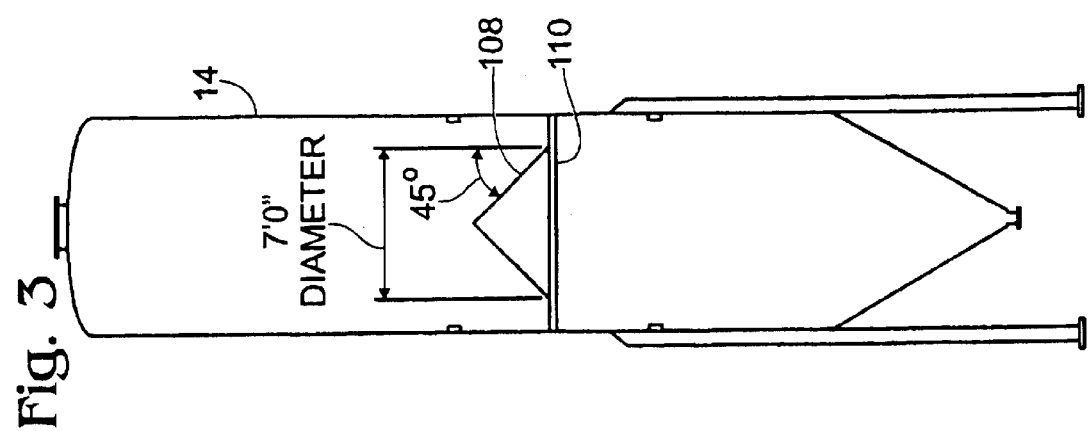

Configuration B. A single conical-shaped baffle 108, as shown in FIG. 3, on a baffle support 110. Baffle 108 has a hollow conical shape that fills up with digester gas as gas is emitted from the processed sludge. The gas-filled cone functions as a solid cone. As flow moves down the plug-flow digester, a parabolic velocity profile is developed with the velocity at the tank wall approaching zero while the velocity at the center of the tank increases. Baffle 108 redirects flow to the perimeter of the tank. Gas is released around the periphery of the baffle once the baffle is initially filled.

Figure 4:
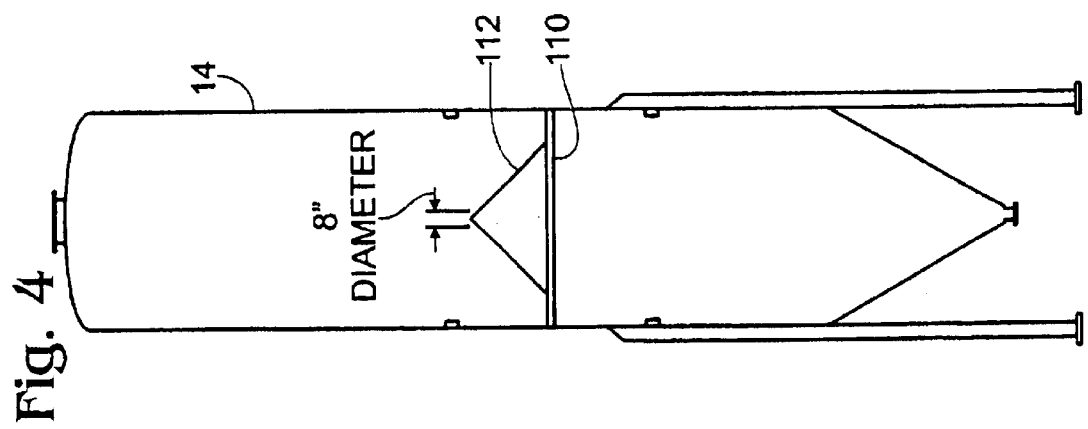

Configuration C. A single conical-shaped baffle 112 with a hole in the center, as shown in FIG. 4. Baffle 112 functions similarly to the Configuration B baffle, with the exception that the gas evolved beneath the baffle is released through a central hole. The gas rising through the hole further discourages the formation of a parabolic velocity profile.

Figure 5:
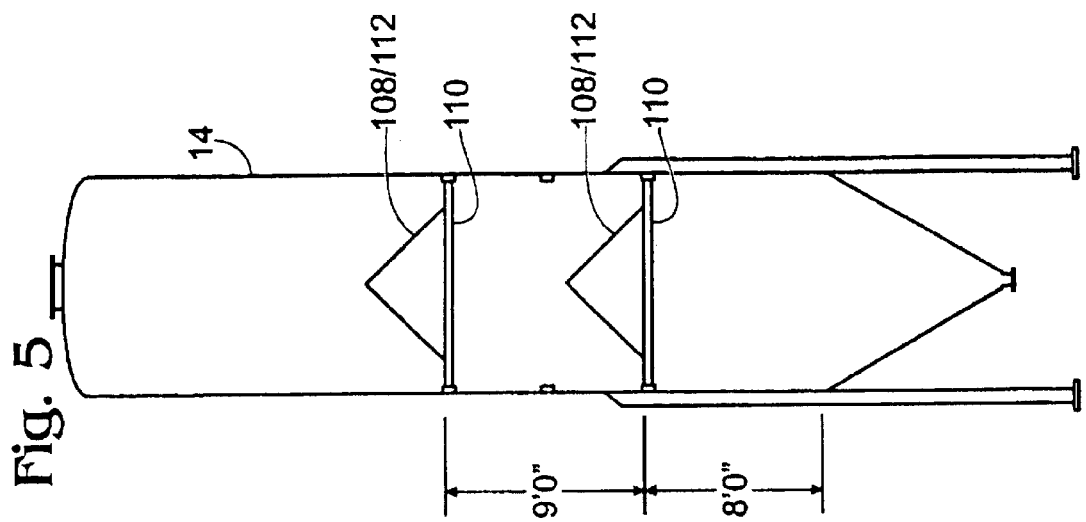
FIGS. 3–5 depicts various baffle embodiments used in a reactor vessel of the invention.

Configuration D. With two baffles of either Configuration B (108) or C (112), as shown in FIG. 5.

The management of sludge produced from wastewater treatment is regulated in the United States of America under 40 CFR Part 503. Treated sludge intended for land application is designated as either Class A or Class B, depending on the pathogen content. Class A biosolids are essentially pathogen-free. Some sludge treatment processes are designated in the regulations as capable of achieving the Class A criteria, or as "processes to further reduce pathogens" (PFRP), but thermophilic anaerobic digestion is not among them. To date, very few thermophilic anaerobic digestion facilities have qualified as Class A other than through the 40 CFR § 503.32(a)(3)—Alternative 1 time and temperature requirements. These requirements are established through the use of an equation that is referred to as the "time-temperature equation." It is understood by the regulated community that the time-temperature requirements cannot be achieved with continuous-flow digesters because of the potential for short-circuiting of the influent sludge to the reactor outlet.

As an alternative, the method of the invention qualifies under 40 CFR § 503.32 (a)(8)—Alternative 6, as an equivalent PFRP. The CBFT$^3$ process configuration must be demonstrated to reduce pathogen densities to Class A levels if it is to be accepted as an equivalent PFRP.

The CBFT$^3$ Treatment System

Figure 6:
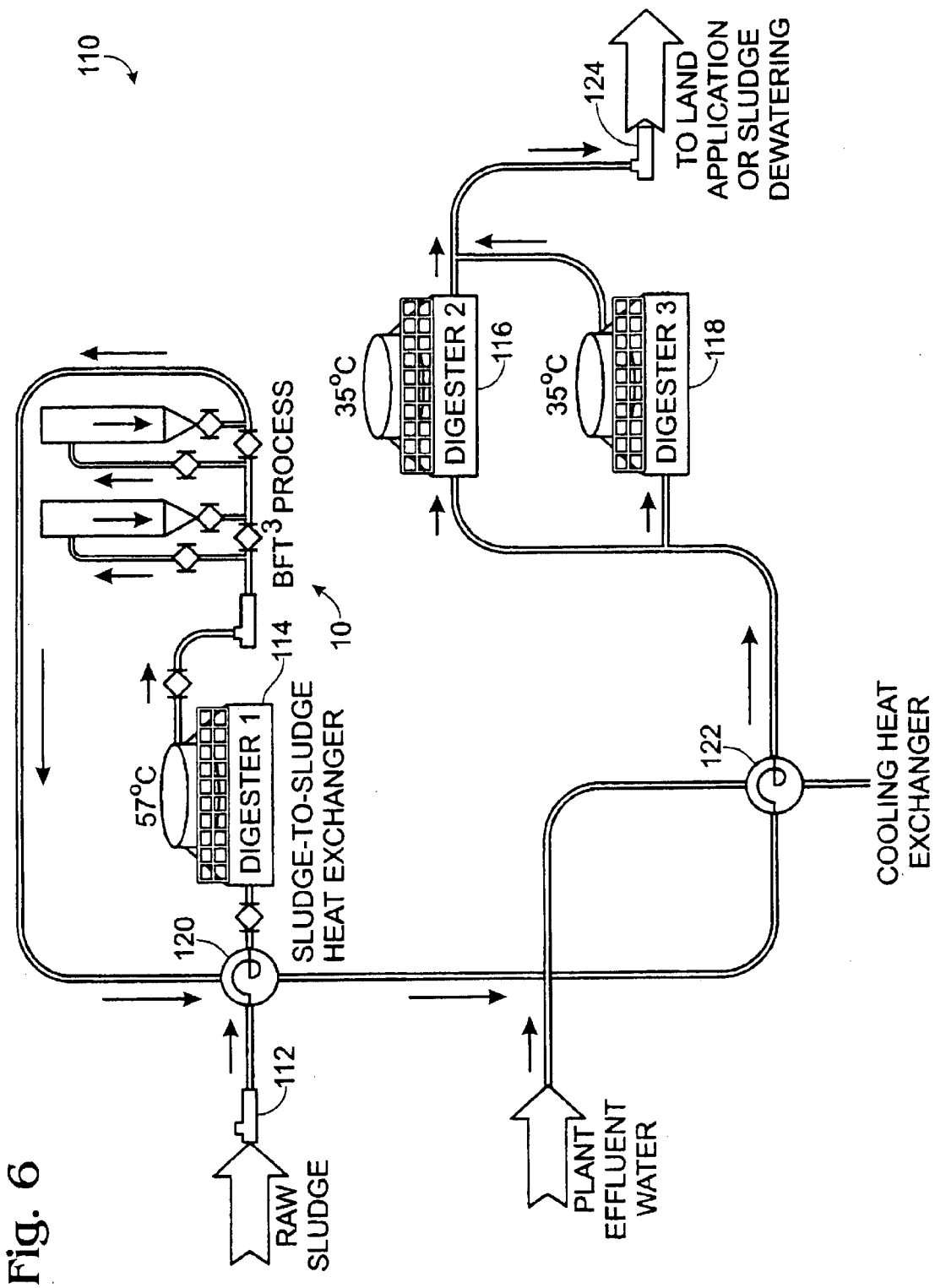
FIG. 6 is a block diagram of a system incorporating the method of the invention.

The CBFT$^3$ embodiment of the complete wastewater sludge treatment method of the invention is depicted generally at 110 in FIG. 6. Raw sludge enters the system at 112 and is directed to a first digester 114, which operates at a specific temperature in a range of between about 51° C. to 60° C., and retains the wastewater sludge, on average, for several, usually, at least four days. From digester 114, the wastewater sludge goes, in this embodiment of the invention, to batch-tank equivalent, plug-flow reactor 10, the second digester, where the wastewater sludge is thermophilically treated at a temperature in a range of between about 51° C. to 60° C. for at least 30 minutes to five hours, at a temperature no more than 2° C. greater than the specific temperature of the thermophilic temperature in the first digester. When thermophilically treated wastewater sludge leaves plug-flow reactor 10, in this embodiment of the invention, it is directed to a third set of digesters, digesters 116, 118, which operate at a temperature of about 35° C., and which hold the treated wastewater sludge for at least about 8 days, up to 30 days. Enroute, the thermophilically treated wastewater sludge passes through a sludge-to-sludge heat exchanger 120, and a cooling heat exchanger 122. Once the wastewater sludge has been treated in digesters 116 and 118, it proceeds to either a land application or to a sludge dewatering operation, 124.

In the BFT$^3$ process definition, the CFSTR must have a mean cell residence time (MCRT) of 4 days. This is the average time as a function of total active volume divided by feed rate. Laboratory-scale testing at 55° C. was conducted using a 4-day MCRT. Testing at 53° C. and 51° C. was conducted at MCRTs of between 5 days and 6 days. The downstream batch (batch tank, second digester) must have a minimum detention time of between 30 minutes and five hours, with the most likely criteria being a minimum detention time of one hour.

In the operation of the CBFT$^3$ system and method of FIG. 6, the first stage CFSTR likely operates at an MCRT of between 7 and 15 days, and the plug-flow reactor operates with minimum detention times of between 0.5 hours and 5 hours. The range on this parameter is much greater because the detention time is much lower than in the CFSTR, and hourly peaking factors are involved. The minimum batch detention time needed for PFRP equivalency, currently presented as "between 0.5 and 5 hours," will be finalized based on discussions with the PEC. The MCRT in the plug-flow reactor may be anywhere from between about 2 hours to 20 hours, depending largely on the character and volumetric flow rate of the waste being treated, the actual operating temperature and the number of plug-flow reactor vessels online.

Whether or not a third digester is required downstream of the BFT$^3$ process units is dependent on what is required reliably to meet vector attraction reduction (VAR) requirements, as defined in 40 CFR § 503.33. Several embodiments of the system may be provided depending on the character of the waste being treated and available existing facilities. There are many treatment facilities that may opt for a simpler alternative VAR approach, other than downstream mesophilic digestion. Downstream mesophilic digestion is one logical choice for retrofit treatment facilities where mesophilic digester tanks are already present, as using mesophilic digestion following the BFT$^3$ process will result in better volatile solids reduction and more capacity to handle increased future sludge flow; and for a treatment plant using the three sets of digester tanks, the energy to be saved from heat recovery is significant and easily pays for the capital cost of the additional mechanical equipment required for heat recovery.

The following five options, and now referring to FIG. 7, identify possible systems for BFT$^3$ to be adapted to satisfy the VAR requirements within 40 CFR § 503 regulation:

Option 1 (Within the BFT$^3$ CFSTR), block 132: If the first stage, i.e., the first digester, is large enough to consistently achieve greater than 38% volatile solids reduction (VSR), the BFT$^3$ process units alone will be capable of meeting the VAR requirements. Achieving at least 38% VSR is defined as a means of meeting the VAR requirement for anaerobically digested sludge under 40 CFR § 503.33-b.1. Thus, no post BFT$^3$ treatment is necessary.

Option 2 (Oversize the downstream batch), block 134: The downstream batch, or equivalent batch, i.e., the second digester, e.g., the plug-flow reactor in some embodiments of the invention, may be oversized to provide considerable MCRT in addition to meeting the minimum detention requirement. In this case, as in Option 1, the VAR requirements may be met in the BFT$^3$ process units alone. An example of this approach may include use of just three large digesters, or reactor vessels, for the downstream batch. Each tank may be sequentially (1) fed for the to-be-determined required batch time, (2) held without feed or discharge for the required batch time, and then (3) discharged for the required batch time. The hold time, without feed or discharge, satisfies the BFT$^3$ downstream batch requirement. For large tanks, only one hour worth of sludge is transferred into each batch tank, rather than the entire tank volume. In this kind of application, potentially large MCRTs and significant VSR are possible in tanks configured to meet the downstream batch time. If the combination of the CFSTR MCRT and the downstream batch MCRT is large enough to consistently achieve greater than 38% VSR, then the VAR requirements may be met by that combination alone. In order to provide a useful Class A product, the pathogen inactivation requirement must be met either concurrently or before the VAR requirements are satisfied. In Options 1 and 2, the two criteria are achieved concurrently. Because the three large batch tank digesters and the initial CFSTR contents are maintained at approximately the same temperature, in excess of the defined minimum temperature stipulated in the BFT$^3$ definition, and with less than a 2° C. temperature elevation between the CFSTR and the downstream batch tanks, the VSR are met concurrently with the pathogen inactivation step and results in a Class A biosolids product being discharged from the BFT$^3$ process units.

Option 3 (Provide additional thermophilic digestion downstream of the BFT$^3$ process), block 136: Under this Option, additional thermophilic anaerobic digestion volume is added downstream of the BFT$^3$ process units. The operational MCRT and temperature of this downstream thermophilic digestion process are not important, provided that the combination of the BFT$^3$ and downstream thermophilic step achieves at least 38% VSR.

Option 4 (Provide mesophilic digestion time downstream of the BFT$^3$ process), block 138: In a manner very similar to Option 3, this Option may achieve the total VAR requirement through a combination of the VSR achieved in the BFT$^3$ process units and the VSR achieved in mesophilic digestion downstream of the BFT$^3$ units. Under this option, the sludge leaving the BFT$^3$ units is cooled to mesophilic temperatures, e.g., 35° C. to 42° C., and digested further in downstream mesophilic digesters. The operational MCRT and temperature of this downstream mesophilic digestion process are not important, provided that the combination of the BFT$^3$ and downstream mesophilic step achieves at least 38% VSR.

Option 5 (Provide some alternative VAR option downstream of BFT$^3$), block 140: 40 CFR § 503 regulation includes a number of alternatives to meet the VAR requirements in addition to achieving 38% VSR in anaerobic digestion. These alternatives are all defined under 40 CFR § 503.33-b. The most likely other means of satisfying the VAR requirements are enumerated herein by sub-paragraph number in the regulation: 2) 40-day additional digestion test; 3) 30-day additional digestion test; 9) subsurface injection of biosolids; or 10) Incorporation into the soil.

Description of Laboratory System

The laboratory system includes a 20 liter (L) (working volume) continuous-flow stirred-tank reactor (CFSTR) and a 4.5 L batch reactor operated under thermophilic anaerobic conditions. The reactors are cylindrical, constructed of stainless steel, and are totally enclosed, except for inlet and outlet ports for feed sludge, treated biosolids, and gas. All inlets and outlets are valved. Each reactor is mixed with a gas-tight mechanical agitator suspended from the reactor headplate. Mixing is continuous in the CFSTR and is continuous in the batch reactor while it is being operated. Both reactors are suspended in an insulated water bath maintained at constant temperature (±0.1° C.) with duplicate precision temperature controllers. Periodic pressure testing has indicated that the reactors are capable of holding a pressure of 5 pounds-per-square-inch gauge (psig), with the mixers on, for at least 24 hours.

Sludge is pumped into the CFSTR intermittently with a cycle of one minute on and a variable amount of off time. The off-time ranged from between about 5.3 to 5.5 minutes for the period of operation. To maintain constant volume, effluent is pumped out of the digester at the same rate and over the same cycle as feed is introduced into the digester. To minimize short-circuiting, the outlet for the feed tube is located near the bottom of the reactor and the inlet for the effluent tube is submerged just below the liquid surface. The feed and effluent pumps are controlled from a computer, which synchronizes the cycles for the two pumps. Average daily flow rates are determined by periodically measuring the cumulative effluent volume and recording the time interval between measurements.

Untreated sludge is stored in a 145 L (nominal) polyethylene tank in a refrigerated cooler kept at 4° C. to 7° C. The reservoir is mixed intermittently (for 30 seconds every hour) with a submersible sump pump modified to discharge through a manifold with openings near each corner of the tank. At intervals of approximately 3.5 days, 20 L of sludge is transferred from the reservoir to a polyethylene carboy, also located in the cooler, which serves as a feed tank for the CFSTR. The feed tank is mixed continuously. A slow stream of argon is passed over the feed tank and reservoir to minimize air entrainment.

Off-gas from the CFSTR is routed through a chilled condenser to remove moisture, then through a pressure regulator and digital gas flow meter. Pressure is maintained at between about 0.1 psig to 0.3 psig. The gas flow meter is calibrated with replicate measurements of gas flow (downstream of the meter) using a bubble flow meter.

For part of the operating period, a side stream of the off-gas (upstream of the flow meter) was routed continuously through a gas chromatograph (GC) sampling loop for periodic analysis by autoinjection. The flow rate through the sampling loop was less than 2% of the total gas flow rate and is accounted for in the gas flow data.

Temperature in each reactor is measured with thermistors suspended in the biosolids. The thermistors are connected to precision electronic thermometers (accuracy of ±0.06° C.) and periodically calibrated against an NIST-traceable thermometer. The water bath is used as the calibration medium.

Gas flow data and temperature readings from the temperature controllers and electronic thermometers are sent to a data acquisition system on a computer and stored in a spreadsheet. Data generally are recorded at intervals of 15 to 30 minutes.

Summary of Operation of the Laboratory Continuous-Flow Stirred Tank (CFSTR) at 55° C.

Operating Conditions. For the test period, sludge was obtained from the SCWRF and the reactors were operated at 55° C. The sludge comprised of a mixture of approximately 55% primary sludge and 45% waste activated sludge. Sludge was shipped once a week in three 20 L carboys in an insulated chest cooler. For each shipment the contents of at least two carboys were combined and processed by pumping through a marine sewage macerator pump, whose impeller also serves as a cutting blade to reduce the size of large solids. The blended sludge was then pumped into the sludge reservoir through a wire-mesh screen having openings of about 0.6 cm. The sludge reservoir held a volume equivalent to the volume fed to the CFSTR over approximately three weeks, which was considered to be sufficient equalization to preclude large step changes in feed composition.

The target hydraulic residence time was 4 days, which was chosen to be conservatively short. Many full-scale plants using or interested in using thermophilic anaerobic digestion will operate at significantly longer residence times.

Pathogen and Indicator Organism Evaluations: The pathogens of interest in sludge include bacteria, enteric viruses, and helminths. Since helminths and enteric viruses are not normally present in domestic sludge at concentrations high enough to measure reliably, the pathogen surrogates *Ascaris suum*, a helminth found in swine which is very similar to the human pathogen *Ascaris lumbricoides* ova, and vaccine-strain poliovirus, were spiked into the feed sludge with each transfer of sludge into the feed tank, e.g., every 3.5 days.

Destruction of the pathogens and potential indicator organisms in the CFSTR was measured by collecting feed and effluent samples on three occasions. Further destruction in the batch reactor was followed on two of those occasions. To perform a batch treatment experiment, i.e., a batch test, approximately 4.5 L of biosolids was transferred anaerobically into the batch reactor. An additional liter of biosolids was collected at the same time to represent a sample of effluent from the CFSTR. Samples were then collected from the batch tank at pre-selected intervals. Transfers and sampling of biosolids were achieved by closing all ports into or out of the reactor, pressurizing the reactor headspace with argon, and opening the desired transfer line.

All effluent biosolids samples were placed in polyethylene bottles, which were closed tightly and immersed in a water/isopropanol bath containing several ice packs to maintain a bath temperature of −10° C. to −15° C. The rate of cooling was measured on several occasions. For a 500 mL sample (a typical aliquot volume) the temperature reached 30° C. within five minutes and 10° C. within 30 minutes. Cooled samples were placed in a cold room and maintained at approximately 5° C. until analysis.

Feed sludge and effluent biosolids were analyzed for the representative pathogens or pathogen surrogates *Ascaris suum*, poliovirus, and *Salmonella*. Samples were also analyzed for potential indicators: fecal coliform, *Clostridium perfringens* spores, somatic coliphages and male-specific coliphages. Details of the microbiological methods are provided later herein.

Other Analyses: Discrete samples of feed sludge and effluent biosolids were also collected for measurement of pH, alkalinity, volatile fatty acids (by titration), total solids, volatile solids (VS), and ammonium. The composition of off-gas from the CFSTR was not analyzed during the early part of the study, but was analyzed during the period of operation represented by the third sampling event. At selected intervals, e.g., generally four to six hours, a gas sample was automatically injected into the GC for analysis of methane and carbon dioxide content. Each gas was calibrated against two known concentrations bracketing the range of measured values.

Results: There were two distinct operating periods over which the CFSTR was operated at 55° C. Feed characteristics over each period are summarized in Table 1, and operating parameters and performance data are summarized in Table 2. The performance data reflect operation at a short hydraulic residence time of approximately four days. For example, solids destruction is lower and residual VFAs higher than would be expected for a digester operated at longer residence times. The pH was in a range that is normal for anaerobic digestion, and effluent ammonium-nitrogen was in the range expected for the influent VS concentration. Gas production per unit VS destroyed was at the high end of the expected range.

TABLE 1

Feed Sludge Characteristics During Operation of the Laboratory CFSTR at 55° C.

| | Value Over Indicated Operating Period [a] | |
|---|---|---|
| Parameter | 15 day treatment | 8 day treatment |
| Solids: | | |
| total, % (wt:wt) | 3.14 ± 0.12 (5) | 2.99 ± 0.13 (3) |
| volatile, % (wt:wt) | 2.36 ± 0.08 (5) | 2.22 ± 0.10 (3) |
| volatile/total, % | 75.4 ± 0.4 (5) | 74.2 ± 0.6 (3) |
| pH | 6.42 ± 0.12 (4) | 6.26 ± 0.19 (3) |
| Alkalinity, mg/L as $CaCO_3$ [b] | | |
| total | 942 ± 194 (4) | 1,300 ± 341 (3) |
| bicarbonate | 67 ± 22 (4) | 93 ± 49 (3) |
| volatile fatty acid (VFA) | 875 ± 207 (4) | 1,210 ± 300 (3) |
| VFAs as acetic acid, mg/L | 1,050 ± 249 (4) | 1,450 ± 360 (3) |
| $NH_4^+$—N, mg/L | 456 ± 67 (5) | 482 ± 65 (2) |

[a] Mean ± standard deviation. Where shown, the number in parentheses is the number of samples. Data for feed samples are for all samples collected during the operating period.
[b] Based on titration of centrifuged effluent biosolids to pH 5.75 (bicarbonate alkalinity) and 4.3 (total alkalinity); VFA alkalinity is the difference between total and bicarbonate alkalinity.

TABLE 2

Operating Parameters and Performance of the Laboratory CFSTR at 55° C.

| | Value Over Indicated Operating Period [a] | |
|---|---|---|
| Parameter | 15 day treatment | 8 day treatment |
| Temperature, ° C. | 55.06 ± 0.04 (556) | 55.00 ± 0.02 (467) |
| Flow, L/d [b] | 5.00 (12) | 4.56 (5) |
| Digester volume, L | 20.1 ± 0.08 (12) | 19.9 ± 0.17 (5) |
| Hydraulic residence time (HRT), days | 4.02 ± 0.02 | 4.37 ± 0.04 |
| Effluent solids: | | |
| total, % (wt:wt) | 2.42 ± 0.05 (4) | 2.19 ± 0.02 (2) |
| volatile, % (wt:wt) | 1.62 ± 0.06 (4) | 1.42 ± 0.02 (2) |
| volatile/total, % | 66.6 ± 1.3 (4) | 65.0 ± 0.6 (2) |
| Solids destruction, % | | |
| total | 22.9 ± 2.8 | 26.7 ± 2.9 |
| volatile | 31.6 ± 1.7 | 35.8 ± 1.7 |
| Effluent pH | 7.39 ± 0.06 (7) | 7.37 ± 0.04 (2) |
| Effluent alkalinity, mg/L as $CaCO_3$ [c] | | |
| total | 2,850 ± 154 (7) | 2,950 ± 156 (2) |
| bicarbonate | 1,520 ± 141 (7) | 1,550 ± 398 (2) |
| volatile fatty acid (VFA) | 1,340 ± 54 (7) | 1,390 ± 242 (2) |
| Effluent VFAs as acetic acid, mg/L | 1,610 ± 65 | 1,670 ± 290 |
| Effluent $NH_4^+$—N, mg/L | 932 ± 57 (5) | 967 ± 41 (2) |
| Gas flow, mL/min | 32.4 ± 4.4 (483) | 26.8 ± 3.2 (607) |
| Gas production: | | |
| $m^3$ per kg VS fed | 0.40 ± 0.05 | 0.38 ± 0.05 |
| $m^3$ per kg VS destroyed | 1.25 ± 0.21 | 1.06 ± 0.17 |

TABLE 2-continued

Operating Parameters and Performance of the Laboratory CFSTR at 55° C.

| | Value Over Indicated Operating Period [a] | |
|---|---|---|
| Parameter | 15 day treatment | 8 day treatment |
| Gas composition: | | |
| $CH_4$, % (vol:vol) | ND [e] | 60.4 ± 0.1 (18) |
| $CO_2$, % (vol:vol) | ND | 36.4 ± 0.4 (18) |

[a] Mean ± standard deviation, except for flow. Where shown, the number in parentheses is the number of samples or number of recorded measurements for electronically acquired data. Effluent data are for samples collected after at least one hydraulic residence time elapsed.
[b] Based on linear correlation between cumulative effluent volume and time; $r^2 = 0.999$ for both operating periods.
[c] Based on titration of centrifuged effluent biosolids to pH 5.75 (bicarbonate alkalinity) and 4.3 (total alkalinity); VFA alkalinity is the difference between total and bicarbonate alkalinity.
[d] Only methane and carbon dioxide were quantified. Most of the remaining gas is believed to be argon and nitrogen, based on observed peaks during gas chromatographic analysis.
[e] ND, not determined.

Results from each pathogen and indicator sampling event for the CFSTR are summarized in Tables 3 through 5. Note that after the second sampling event was completed, the quantity of *Ascaris* ova and poliovirus spiked into the feed sludge was increased by an order of magnitude, which is reflected as higher measured feed concentrations of these species for the third sampling event (Table 5). For *Ascaris* ova the concentrations of both the viable and non-viable (unembryonated) ova are reported. The $\log_{10}$ density reductions of each pathogen or indicator for the three sampling events are summarized in Table 6.

TABLE 3

Pathogen and Indicator Data for the CFSTR

| | Concentration ($\log_{10}$/g TS) [a] | | |
|---|---|---|---|
| Organism | Feed [b] | Effluent [c] | $\log_{10}$ Reduction |
| *Ascaris suum* | | | |
| viable ova | 2.43 | <0.55 | >1.88 |
| unembryonated ova | 1.59 | 2.71 | NA [d] |
| Poliovirus | | | |
| pfu [e] | 3.08 | <0.70 | >2.38 |
| MPN | 2.75 | <-0.23 | >2.98 |
| Salmonella | 3.06 | <-0.89 | >3.95 |
| *Clostridium perfringens* | 5.74 | 6.2 | NR [f] |
| Somatic coliphages | 4.81 | 4.77 | 0.04 |
| Male-specific coliphages | 4.06 | 2.03 | 2.03 |
| Fecal coliform | 7.47 | 3.17 | 4.30 |

[a] All concentrations were measured as most-probable-number (MPN) except where indicated and were normalized per g total solids (dry weight).
[b] Feed sample was from a batch prepared on day 7 of 15 day treatment
[c] Values shown as "less than" were below the indicated detection limit.
[d] NA, not applicable.
[e] pfu, plaque-forming unit.
[f] NR, no removal.

TABLE 4

Pathogen and Indicator Data for the CFSTR Sampling Period on days 14–15

| | Concentration ($\log_{10}$/g TS) | | | |
|---|---|---|---|---|
| Organism | Feed 1 [a] | Feed 2 [b] | Effluent | $\log_{10}$ Reduction [c] |
| *Ascaris suum* | | | | |
| viable ova | 2.46 | 2.56 | <0.27 | >2.24 |
| unembryonated ova | 1.59 | 1.67 | 2.39 | NA |
| Poliovirus | | | | |
| pfu | 2.46 | 2.65 | <0.63 | >1.93 |
| MPN | 2.65 | 2.39 | <-0.40 | >2.92 |
| Salmonella | 2.79 | 3.66 | <-0.67 | >3.90 |
| *Clostridium perfringens* | 6.55 | 6.41 | 6.28 | 0.20 |
| Somatic coliphages | >6.71 | 4.00 | 3.95 | >0.86 |
| Male-specific coliphages | 4.74 | 4.96 | 2.43 | 2.42 |
| Fecal coliform | 7.99 | 7.55 | 3.04 | 4.73 |

[a] Feed sample was from a batch prepared on day 11 of 15 day treatment
[b] Feed sample was from a batch prepared on day 14 of 15 day treatment
[c] Based on the mean of the two feed samples. All other notes as in Table 3.

TABLE 5

Pathogen and Indicator Data for the CFSTR Sampling Period on days 14–15 [a]

| | Concentration ($\log_{10}$/g TS) | | |
|---|---|---|---|
| Organism | Feed | Effluent [b] | $\log_{10}$ Reduction |
| *Ascaris suum* | | | |
| viable ova | 3.02 | <0.67 | >2.35 |
| unembryonated ova | 2.70 | 2.93 | NA |
| Poliovirus (pfu) | 4.48 | <0.19 | >4.29 |
| Somatic coliphages | 4.73 | 3.70 | 1.03 |
| Male-specific coliphages | 4.45 | 1.84 | 2.61 |

[a] Notes are as in Table 3.

TABLE 6

Summary of Pathogen and Indicator Reductions Across the CFSTR

| | $\log_{10}$ Reduction at Indicated Sampling Event | | |
|---|---|---|---|
| Organism | day 7–8 of 15 | days 14–15 | days 7–8 of 8 |
| *Ascaris suum* | >1.88 | >2.24 | >2.35 |
| Poliovirus | | | |
| pfu | >2.38 | >1.93 | >4.29 |
| MPN | >2.98 | >2.92 | |
| Salmonella | >3.95 | >3.90 | ND [a] |
| *Clostridium perfringens* | NR [b] | 0.20 | ND |
| Somatic coliphages | 0.04 | 0.86 | 1.03 |
| Male-specific coliphages | 2.03 | 2.42 | 2.61 |
| Fecal coliform | 4.30 | 4.73 | ND |

[a] ND, not determined.
[b] NR, no removal.

Results from each of the two batch tests are summarized in Tables 7 and 8. For each of these tests, the data shown for the initial (time zero) sample represent concentrations in the CFSTR effluent. For both tests, concentrations of viable *Ascaris* ova poliovirus, and *Salmonella* were below detection limits in all samples (not shown), consistent with the lack of detection of these species in the CFSTR effluent. Detection limits were of the same magnitude shown in Tables 3–5. Concentrations of unembryonated *Ascaris* ova are shown to illustrate that non-viable ova were recoverable in treated biosolids samples at concentrations above 2 $\log_{10}$/g total solids (TS) at all sampling times.

TABLE 7

Results from the Batch Test Conducted on day 8 of 15

Concentration of Indicated Organism ($\log_{10}$/g TS)

| Time (hr) | Unembry- onated *Ascaris* ova | *Clostridium perfringens* | Male- specific coliphages | Somatic coliphages | Fecal coliform |
|---|---|---|---|---|---|
| 0 | 2.71 | 6.20 | 2.03 | 4.77 | 3.17 |
| 1 | 2.30 | 6.35 | <1.95 | 3.80 | 3.13 |
| 2 | 2.15 | 5.38 | <1.82 | 3.75 | 2.10 |
| 4 | 2.09 | 5.77 | <1.69 | 3.29 | 0.69 |
| 8 | ND | 6.00 | <1.61 | 3.78 | 0.91 |

TABLE 8

Results from the Batch Test Conducted on day 15

Concentration of Indicated Organism ($\log_{10}$/g TS)

| Time (hr) | Unembry- onated *Ascaris* ova | *Clostridium perfringens* | Male- specific coliphages | Somatic coliphages | Fecal coliform |
|---|---|---|---|---|---|
| 0 | 2.39 | 6.28 | 2.43 | 3.95 | 3.04 |
| 1 | 2.97 | 6.77 | 2.26 | 3.77 | 3.36 |
| 2 | 2.65 | 6.20 | 2.57 | 3.62 | 2.02 |
| 4 | 2.76 | 6.34 | 1.94 | 3.54 | 1.75 |
| 8 | 2.42 | 6.21 | 2.05 | 3.35 | 1.70 |

Thermophilic anaerobic digestion at 55° C. and a four-day hydraulic residence time in a CFSTR was able to achieve at least a two-log reduction in the density of viable *Ascaris suum* ova, at least a three-log reduction in the density of poliovirus, and nearly a four-log reduction in the density of *Salmonella*. None of these species was detected in the CFSTR effluent on any of the sampling events. For *Ascaris* ova the data on unembryonated ova reinforce the destruction observed by measuring viable ova. The data obtained at 55° C. appears to meet the target densities of removal for *Ascaris* ova and poliovirus required to achieve PFRP equivalency.

Of the potential indicators, fecal coliform was removed to the greatest extent (greater than a four-log reduction) with a further one-log removal during batch treatment for two hours. Concentrations of *Clostridium perfringens* were essentially unchanged across the CFSTR, a result that was reinforced in batch incubations at 55° C. for an additional eight hours. It therefore appears that *C. perfringens* spores are not useful indicators of pathogen destruction by thermophilic anaerobic digestion at temperatures at or below 55° C. The coliphages were removed in the CFSTR but not to the same extent as poliovirus. Male-specific coliphages were removed more extensively than somatic coliphages across the CFSTR, although this difference was not apparent in subsequent batch treatment of the CFSTR effluent. Either of these classes of bacteriophage may be conservative indicators of enteric virus destruction under thermophilic conditions.

Results of the Spiked-Batch Tests at 55° C.

Destruction of *Ascaris suum* ova, poliovirus, and the potential indicators somatic coliphage and male-specific coliphage was evaluated in a lab-scale, batch anaerobic digester operated at 55° C. Destruction of these organisms was followed after spiking them into the batch reactor. To distinguish these experiments from the other experiments designed to evaluate the BFT$^3$ concept, these experiments are referred to as spiked-batch tests.

The physical description of the batch reactor is similar to that of the continuous-flow reactor (CFSTR) described previously herein, except the working volume in the batch reactor is approximately 4.5 L. The batch reactor was filled by anaerobic transfer of biosolids from the CFSTR, with an extra liter of biosolids collected at the same time to provide a sample of effluent from the CFSTR. This sample also approximates the initial condition in the batch reactor prior to spiking.

A 100 mL aliquot of spiking material was prepared by mixing concentrated stocks of *Ascaris* ova poliovirus, and coliphages into untreated sludge (feed sludge for the CFSTR). The approximate volumes were 60 mL of sludge and 40 mL (combined) of the pathogen and coliphage stocks. Target amounts of *Ascaris* ova and poliovirus added in the spike were $4 \times 10^5$ ova and $10^6$ plaque-forming units (pfu), respectively, which corresponded to initial concentrations in the reactor of 3.6 and 4.0 $\log_{10}$gram total solids (TS), respectively.

The spiking material was mixed in a beaker, covered with parafilm, and stored cold overnight. It was removed from the refrigerator two to three hours before initiating the batch test and allowed to approach room temperature, then was warmed slowly, with slow mixing, on a hot-plate. For the first test, the spiking material was warmed to 40° C. and for the second test, it was warmed to 36° C. The spiking material was removed from the hot-plate immediately after reaching the target temperature, then poured into the batch reactor through a wide port. The port was then closed and the reactor contents allowed to mix for 90 seconds before collecting the first sample. This sample is referred to as the "time zero" sample. For the first test, the initial mixing probably was not sufficient to have mixed the spiking material instantaneously. Therefore, just before obtaining a sample at 15 minutes, the mixer intensity was increased to a level subsequently confirmed to provide adequate mixing of the reactor contents.

Samples were collected at 0.25, 0.5, 1, 2, 4, 8 and 24 hours after the time zero sample. All samples were cooled and processed as previously described, except the maximum aliquot volume was approximately 300 mL per sample bottle. The total solids concentration was measured at each time point; the initial TS content was 20 grams/liter (g/L) to 21 g/L (dry weight) and by the 8-hr sample the TS was 12 g/L to 14 g/L. For both tests, the 24-hr sample had significantly higher solids content than all earlier samples, suggesting that the small volume remaining in the reactor between eight and 24 hours was not mixed well. Such lack of mixing, however, is not believed to have significantly influenced the results.

Results from the two spiked-batch tests are reported in Tables 9 and 10. Data for the time zero sample for the first test are ambiguous because of poor initial mixing conditions. Nevertheless, the data in Table 9 indicate that both poliovirus and *Ascaris* ova were destroyed to below detection limits within 15 minutes of batch treatment at 55° C.

TABLE 9

Results from First Spiked-batch Test

Concentration of Indicated Organism (Log$_{10}$/g TS) [a]

| Time (hours) | Ascaris ova | | Poliovirus | Coliphage [b] | |
|---|---|---|---|---|---|
| | viable | non-viable | | Somatic | Male-specific |
| 0 | <0.72 | 3.03 | <−0.49 | 4.04 | 1.62 |
| 0.25 | <0.89 | 3.08 | <−0.49 | ND [c] | 1.18 |
| 0.5 | <0.74 | 3.13 | <−0.44 | 3.77 | 0.90 |
| 1 | <0.87 | 3.42 | <−0.59 | 3.71 | 1.32 |
| 2 | ND | ND | <−0.53 | 3.91 | 1.42 |
| 4 | ND | ND | <−0.13 | 3.55 | 0.79 |
| 8 | ND | ND | <−0.11 | 3.96 | 1.34 |
| 24 | ND | ND | ND | 3.28 | 0.77 |

[a] Concentrations of poliovirus were measured as pfu and concentrations of coliphage were measured as most-probable-number (MPN). All concentrations were normalized per g TS (dry weight).
[b] The concentrations of somatic and male-specific coliphages before spiking the reactor were 3.69 and 1.84 log$_{10}$ MPN/g TS, respectively.
[c] ND, not determined.

Results from the first spiked-batch test were reinforced in the second test (Table 10), for which the initial mixing was adequate. In this case, poliovirus was removed to below detection limits even in the time zero sample. Viable *Ascaris* ova were recovered in both the time zero and 15-minute samples, but were below detection limits by 30 minutes.

TABLE 10

Results from Second Spiked-batch Test [a]

Concentration of Indicated Organism (Log$_{10}$/g TS)

| Time (hours) | Ascaris ova | | Poliovirus | Coliphage | |
|---|---|---|---|---|---|
| | viable | non-viable | | Somatic | Male-specific |
| 0 | 2.56 | 2.89 | <0.01 | 4.66 | 1.65 |
| 0.25 | 1.11 | 2.97 | <0.01 | ND | 1.21 |
| 0.5 | <0.34 | 3.01 | <0.02 | 3.95 | 0.96 |
| 1 | <0.57 | 2.97 | <0.11 | 3.76 | 1.37 |
| 2 | ND | ND | <0.06 | 4.07 | 1.46 |
| 4 | ND | ND | <0.23 | 4.14 | 0.81 |
| 8 | ND | ND | <0.09 | 3.32 | 1.44 |
| 24 | ND | ND | ND | 2.91 | 0.86 |

[a] Notes are as in Table 9.

The coliphages did not decline in a consistent pattern in either of the tests. In both tests, male-specific coliphage concentrations seemed to increase and decrease alternately in consecutive samples, a pattern that was quantitatively reproducible (compare concentrations at each time point for the two tests). Unfortunately, spiking did not have the desired effect of increasing coliphage concentrations well above the background concentrations present in the CFSTR biosolids used to fill the batch tank. The somatic coliphage concentration increased above background by less than one log$_{10}$ after spiking and the male-specific coliphage concentration did not increase at all. Thus, for the male-specific coliphages these batch tests are more indicative of further treatment of the CFSTR effluent for 24 hours than they are of reductions from initial concentrations that might be found in untreated sludge.

Figure 8:
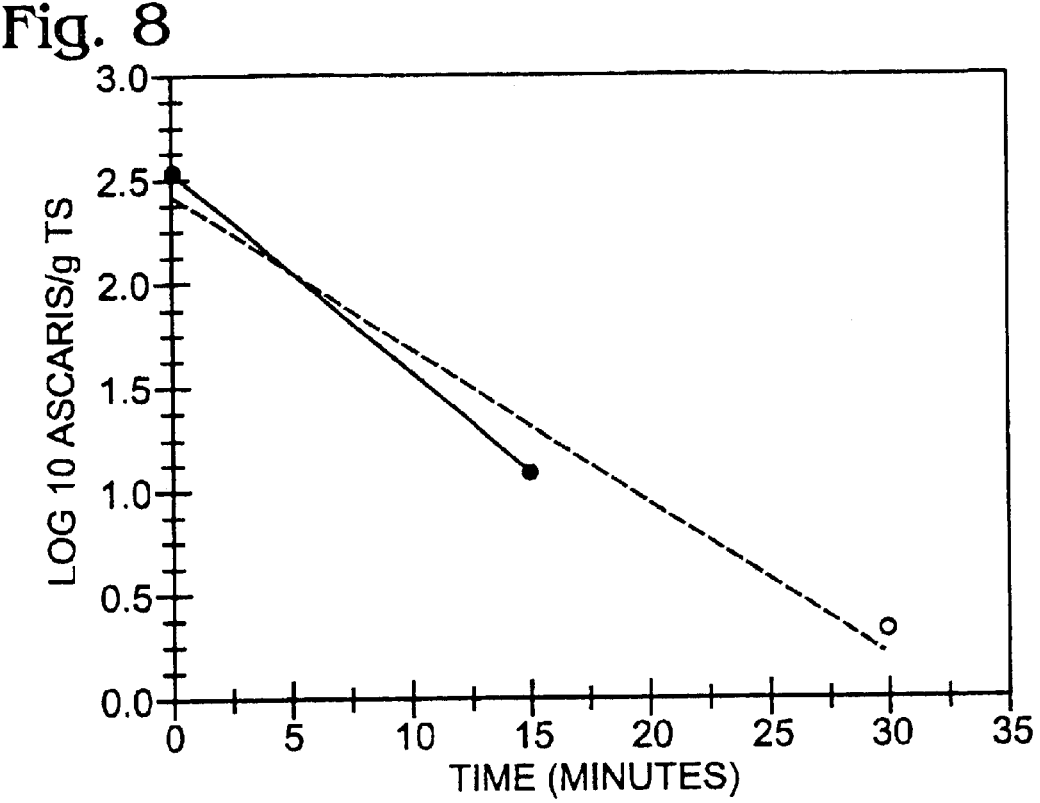
FIG. 8 is a plot of *Ascaris* ova data from a 55° C. spiked-batch test.

The spiked-batch tests illustrate that poliovirus density can be reduced by at least 3 log$_{10}$/g TS very rapidly at 55° C. and that *Ascaris* ova density can be reduced by at least 2 log$_{10}$/g TS within 30 minutes at 55° C. The data from the second test can be used to estimate a rate coefficient for *Ascaris* ova destruction at 55° C. Depending on whether the detection limit for the 30-minute sample is used as a data point for fitting, the first-order rate coefficient is between 10 hr$^{-1}$ and 13 hr$^{-1}$ (240 d$^{-1}$ and 320 d$^{-1}$), as shown in FIG. 8, which is a plot of *Ascaris* ova data from the second spiked-batch test. The open symbol represents a value below the detection limit. Lines represent linear fits to the data for either the first two points (solid line) or all three points (dashed line).

Summary of Operation of the Laboratory Continuous-Flow Stirred Tank (CFSTR) at 53° C.

Operating Conditions. Sludge properties and handling were as described for testing at 55° C. The target hydraulic retention time (HRT) at 53° C. was between 5.5 and 6 days, which is higher than the HRT when the digester was evaluated at 55° C., but still conservatively short.

The period of operation at 53° C. was 31 days. For the process performance parameters other than pathogen or indicator organism destruction, the change in temperature appeared to have a negligible influence on performance. Therefore, data for these parameters in the effluent are reported for all samples collected after one residence time elapsed. Feed data are reported for the entire operating period.

Pathogen and Indicator Organism Evaluations: Feed sludge was amended with the pathogen surrogates *Ascaris suum* and vaccine-strain poliovirus, as described in connection with the 55° C. testing.

Destruction of the pathogens and potential indicator organisms in the CFSTR was measured by collecting feed and effluent samples on four occasions. Further destruction in the batch reactor was followed on two of those occasions. This report summarizes the pathogen and indicator organism data for four feed and effluent sampling events and two batch tests.

Unlike the period of operation at 55° C., spiking of the pathogen surrogates was consistent throughout the period of operation at 53° C. Consequently, data may be pooled for pathogen and indicator removal across the CFSTR. Geometric means (means of log$_{10}$ values) of feed and effluent concentrations are used. Other analyses were conducted as described in connection with the 55° C. testing.

Results: Feed characteristics over the operating period are summarized in Table 11, and operating parameters and performance data are summarized in Table 12. As with operation at 55° C., the performance data reflect operation at a short hydraulic residence time (5.8 days). This residence time is longer than was used at 55° C. (4.0 days), resulting in somewhat greater volatile solids destruction (39% vs. 32%). Other effluent characteristics were very similar to those reported for operation at 55° C.

TABLE 11

Feed Sludge Characteristics During Operation of the Laboratory CFSTR at 53° C.

| Parameter | Value [a] |
|---|---|
| Solids: | |
| total, % (wt:wt) | 2.72 ± 0.24 (7) |
| volatile, % (wt:wt) | 2.04 ± 0.19 (7) |
| volatile/total, % | 75.1 ± 1.1 (7) |
| pH | 6.21 ± 0.20 (7) |
| Alkalinity, mg/L as CaCO$_3$ [b] | |
| total | 1,429 ± 448 (7) |
| bicarbonate | 80 ± 75 (7) |
| volatile fatty acid (VFA) | 1,349 ± 449 (7) |

TABLE 11-continued

Feed Sludge Characteristics During Operation of the Laboratory CFSTR at 53° C.

| Parameter | Value [a] |
|---|---|
| VFAs as acetic acid, mg/L | 1,619 ± 539 (7) |
| $NH_4^+$—N, mg/L | 606 ± 31 (7) |

[a] Mean ± standard deviation. The number of samples is in parentheses.
[b] Based on titration of centrifuged effluent biosolids to pH 5.75 (bicarbonate alkalinity) and 4.3 (total alkalinity); VFA alkalinity is the difference between total and bicarbonate alkalinity.

TABLE 12

Operating Parameters and Performance of the Laboratory CFSTR at 53° C.

| Parameter | Value [a] |
|---|---|
| Temperature, ° C. | 52.98 ± 0.04 (3,061) |
| Flow, L/d [b] | 3.46 (12) |
| Digester volume, L | 20.0 ± 0.28 (9) |
| Hydraulic residence time (HRT), days | 5.79 ± 0.08 |
| Effluent solids: | |
| total, % (wt:wt) | 1.92 ± 0.05 (6) |
| volatile, % (wt:wt) | 1.26 ± 0.03 (6) |
| volatile/total, % | 65.4 ± 0.6 (6) |
| Solids destruction, % | |
| total | 29.5 ± 2.7 |
| volatile | 38.6 ± 3.7 |
| Effluent pH | 7.34 ± 0.06 (6) |
| Effluent alkalinity, mg/L as $CaCO_3$ [c] | |
| total | 3,380 ± 334 (6) |
| bicarbonate | 1,770 ± 96 (6) |
| VFA | 1,610 ± 270 (6) |
| Effluent VFAs as acetic acid, mg/L | 1,940 ± 326 |
| Effluent $NH_4^+$—N, mg/L | 1,030 ± 52 (6) |
| Gas flow, mL/min | 24.9 ± 2.1 (2,217) |
| Gas production: | |
| $m^3$ per kg VS fed | 0.51 ± 0.06 |
| $m^3$ per kg VS destroyed | 1.31 ± 0.27 |
| Gas composition: [d] | |
| $CH_4$, % (vol:vol) | 62.0 ± 1.4 (85) |
| $CO_2$, % (vol:vol) | 32.3 ± 0.7 (85) |

[a] Mean ± standard deviation, except for flow. Where shown, the number in parentheses is the number of samples or number of recorded measurements for electronically acquired data.
[b] Based on linear correlation between cumulative effluent volume and time; $r^2 = 0.9997$.
[c] Based on titration of centrifuged effluent biosolids to pH 5.75 (bicarbonate alkalinity) and 4.3 (total alkalinity); VFA alkalinity is the difference between total and bicarbonate alkalinity.
[d] Only methane and carbon dioxide were quantified. Most of the remaining gas is believed to be argon and nitrogen, based on observed peaks during gas chromatographic analysis.

Results for pathogens and indicators in the feed sludge and effluent from the CFSTR are provided in Table 13. Results from each of the two batch tests are summarized in Tables 14 and 15. For each of these tests, the data shown for the initial (time zero) sample represent concentrations in the CFSTR effluent. For both tests, concentrations of viable *Ascaris* ova and poliovirus were below detection limits in all samples (not shown), consistent with the lack of detection of these species in the CFSTR effluent. Detection limits were of the same magnitude shown in Table 13.

TABLE 13

Pathogen and Indicator Data for the CFSTR at 53° C.

| | Concentration ($log_{10}/g$ TS) [a] | | $Log_{10}$ |
|---|---|---|---|
| Organism | Feed [b] | Effluent [c] | Reduction |
| *Ascaris suum* | | | |
| viable ova | 2.64 ± 0.13 | <0.46 ± 0.06 | >2.18 |
| unembryonated ova | 2.36 ± 0.14 | 3.04 ± 0.07 | NA [d] |
| Poliovirus | 4.69 ± 0.10 | <0.33 ± 0.10 | >4.36 |
| Salmonella | 2.15 ± 0.27 | <0.01 ± 0.38 | >2.14 |
| *Clostridium perfringens* | 6.28 ± 0.25 | 6.18 ± 0.34 | NR [e] |
| Somatic coliphages | 4.49 ± 0.47 | 3.74 ± 0.52 | 1.15 ± 0.46 |
| Male-specific coliphages | 3.31 ± 0.41 | 2.17 ± 0.04 | 1.32 ± 0.43 |
| Fecal coliform | 6.80 ± 0.16 | 1.91 ± 0.20 | 4.89 ± 0.26 |

[a] All concentrations were measured as most-probable-number (MPN) except for poliovirus (measured as plaque-forming units, pfu) and Ascaris ova (measured as individual eggs).
[b] Mean and standard deviations of five samples for Ascaris ova poliovirus, somatic coliphages and male-specific coliphages. Mean and standard deviation of three samples for the other organisms.
[c] Mean and standard deviation of four samples for Ascaris ova poliovirus, somatic coliphages and male-specific coliphages. Mean and standard deviation of two samples for the other organisms. Values shown as "less than" were below the indicated mean detection limit except for Salmonella, for which one of the two samples was above the detection limit (corresponding to an effluent concentration of 0.28 $log_{10}$/g TS).
[d] NA, not applicable.
[e] NR, no removal.

TABLE 14

Results from the Batch Test

| | Concentration at Indicated Time ($log_{10}/g$ TS) | | | | |
|---|---|---|---|---|---|
| Organism | 0 | 1 hr | 3 hr | 9 hr | 24 hr |
| Unembryonated *Ascaris* ova | 3.11 | 3.03 | ND [a] | ND | ND |
| Salmonella | 0.28 | <-0.28 | <-0.27 | <-0.13 | <-0.04 |
| *Clostridium perfringens* | 5.94 | 6.08 | 6.41 | 6.20 | 6.42 |
| Somatic coliphages | 3.18 | 3.40 | 3.19 | 3.56 | 4.06 |
| Male-specific coliphages | 2.18 | 1.93 | 1.01 | 1.16 | 1.79 |
| Fecal coliform | 2.05 | <0.70 | <0.71 | <0.86 | <0.94 |

[a] ND, not determined

TABLE 15

Results from the First Batch Test

| | Concentration at Indicated Time ($log_{10}/g$ TS) | | | | |
|---|---|---|---|---|---|
| Organism | 0 | 1 hr | 3 hr | 9 hr | 24 hr |
| Unembryonated *Ascaris* ova | 3.02 | ND | ND | ND | ND |
| Salmonella | <-0.26 | <-0.25 | <-0.24 | <-0.14 | <0.02 |
| *Clostridium perfringens* | 6.42 | 6.21 | 6.12 | 6.07 | 5.48 |
| Somatic coliphages | 3.42 | 3.85 | 3.65 | 3.32 | 3.48 |
| Male-specific coliphages | 2.20 | 1.62 | 1.48 | 1.80 | 1.60 |
| Fecal coliform | 1.77 | <0.74 | <0.74 | <0.84 | <1.00 |

[a] ND, not determined

For the two batch tests several of the organisms appear to increase in concentration with time. This apparent anomaly results mostly from reporting concentrations per unit solids, which declined substantially over the course of the 24-hour batch tests. Concentrations of the organisms are first measured per unit volume, then converted to a value normalized by dry weight of solids. Trends in the organism concentrations during the batch tests are more understandable when reported per unit volume, as shown in Tables 16 and 17.

TABLE 16

Results from the Batch Test Conducted with Concentrations Normalized by Volume

| | Concentration at Indicated Time ($\log_{10}$/mL) | | | | |
|---|---|---|---|---|---|
| Organism | 0 | 1 hr | 3 hr | 9 hr | 24 hr |
| Salmonella | −1.43 | <−1.98 | <−1.98 | <−1.98 | <−1.98 |
| Clostridium perfringens | 4.23 | 4.38 | 4.70 | 4.34 | 4.48 |
| Somatic coliphages | 1.48 | 1.70 | 1.48 | 1.70 | 2.11 |
| Male-specific coliphages | 0.48 | 0.23 | −0.70 | −0.70 | −0.15 |
| Fecal coliform | 0.34 | <−1.0 | <−1.0 | <−1.0 | <−1.0 |

TABLE 17

Results from the Batch Test Conducted with Concentrations Normalized by Volume

| | Concentration at Indicated Time ($\log_{10}$/mL) | | | | |
|---|---|---|---|---|---|
| Organism | 0 | 1 hr | 3 hr | 9 hr | 24 hr |
| Salmonella | <−1.98 | <−1.98 | <−1.98 | <−1.98 | <−1.98 |
| Clostridium perfringens | 4.70 | 4.48 | 4.38 | 4.23 | 3.48 |
| Somatic coliphages | 1.70 | 2.11 | 1.90 | 1.48 | 1.48 |
| Male-specific coliphages | 0.48 | −0.12 | −0.26 | −0.05 | −0.40 |
| Fecal coliform | 0.04 | <−1.0 | <−1.0 | <−1.0 | <−1.0 |

The data obtained to date indicate that thermophilic anaerobic digestion at 53° C. and a 5.8-day hydraulic residence time in a CFSTR was able to achieve at least a two-log reduction in viable Ascaris suum ova and at least a four-log reduction in poliovirus. The reduction of Salmonella at 53° C. appears to be lower than that obtained at 55° C., with one effluent sample having measurable Salmonella at 0.28 $\log_{10}$/g TS; this concentration corresponds to about a two-log reduction relative to the feed concentration. Neither Ascaris suum ova nor poliovirus was detected in the CFSTR effluent on any of the four sampling events. For Ascaris suum ova, the data on unembryonated ova in the CFSTR effluent reinforce the destruction observed by measuring viable ova. The data obtained at both 53° C. and 55° C. appear to meet the target densities of removal for Ascaris ova and poliovirus required to achieve PFRP equivalency.

Consistent with the results at 55° C., fecal coliform was removed to the greatest extent among the indicators (nearly a five-log reduction) with a further one-log removal during batch treatment for one hour. As at 55° C., concentrations of Clostridium perfringens were essentially unchanged across the CFSTR. There appeared to be no removal during an additional 24 hours of batch treatment in one batch test, while in the other batch test there was about a one-log removal of C. perfringens after 24 hours. Overall, these data further support a conclusion that C. perfringens spores are not useful indicators of pathogen destruction by thermophilic anaerobic digestion at temperatures at or below 55° C.

Both somatic and male-specific coliphages were removed by slightly over one-log across the CFSTR. The removal of somatic coliphages was similar to that observed at 55° C., but the removal of male-specific coliphages was about one-log lower at 53° C. than at 55° C., despite the longer retention time at 53° C. This finding may suggest that male-specific coliphages are more temperature sensitive than somatic coliphages and thus may be a more useful indicator of pathogen destruction in this temperature range. It should be noted, however, that the concentration of male-specific coliphage was one-log lower in the feed sludge during operation at 53° C. than at 55° C., while the effluent concentrations were the same at the two different temperatures. Data on the coliphages for the feed and CFSTR effluent are compared in Table 18. Similar to the results at 55° C., there was no further removal of somatic coliphages during 24 hours of batch treatment and only modest (less than one-log) removal of male-specific coliphages during batch treatment.

TABLE 18

Comparison of Coliphage Data for the CFSTR at 55° C. and 53° C.

| | Concentration ($\log_{10}$/g TS) [a] | |
|---|---|---|
| Coliphage group | Feed | Effluent |
| Somatic: | | |
| 55° C. | 4.51 ± 0.45 (3) [b] | 4.12 ± 0.53 (3) |
| 53° C. | 4.49 ± 0.47 (5) | 3.74 ± 0.52 (4) |
| Male-specific: | | |
| 55° C. | 4.55 ± 0.39 (4) | 2.10 ± 0.30 (3) |
| 53° C. | 3.31 ± 0.41 (5) | 2.17 ± 0.04 (4) |

[a] Number of samples is in parentheses.
[b] One outlier (abnormally high value) omitted.

Results of Spiked-Batch Testing at 53° C.

Destruction of Ascaris suum ova, poliovirus, and the potential indicators somatic coliphage and male-specific coliphage was evaluated in a lab-scale, batch anaerobic digester operated at 53° C. Destruction of these organisms was followed after spiking them into the batch reactor. To distinguish these experiments from the other experiments designed to evaluate the BFT[3] concept, these experiments are referred to as spiked-batch tests.

The physical description of the batch reactor is similar to that of the continuous-flow reactor (CFSTR) provided earlier herein, except the working volume in the batch reactor is approximately 4.5 L. The batch reactor was filled by anaerobic transfer of biosolids from the CFSTR, with an extra liter of biosolids collected at the same time to provide a sample of effluent from the CFSTR. This sample also approximates the initial condition in the batch reactor prior to spiking. Unlike in the experiments designed to evaluate the BFT[3] concept, a significant amount of time (one to two hours) elapsed between first filling the batch reactor and initiation of the spiked-batch test. This amount of time was needed to complete preparations for the spiked-batch test and to allow the batch reactor temperature to stabilize before spiking the reactor.

A 100 mL aliquot of spiking material was prepared by mixing concentrated stocks of Ascaris ova poliovirus, and coliphages (concentrated from domestic wastewater by membrane filtration) into untreated sludge, e.g., feed sludge for the CFSTR. The approximate volumes were 60 mL of sludge and 40 mL (combined) of the pathogen and coliphage stocks.

The spiking material was mixed in a beaker, covered with parafilm, and stored cold overnight. It was removed from the refrigerator two to three hours before initiating the batch test and allowed to approach room temperature, then was warmed slowly, with slow mixing, to 35° C. on a hot-plate. The spiking material was removed from the hot-plate immediately after reaching the target temperature, then poured into the batch reactor through a wide port. The port was then closed and the reactor contents allowed to mix for 90 seconds before collecting the first sample. This sample is referred to as the "time zero" sample.

Samples were collected at 0.17, 0.5, 1, 2, 4, 8 and 24 hours after the time zero sample. All samples were cooled and processed as described earlier herein, except the maximum aliquot volume was approximately 300 mL per sample bottle. The total solids concentration was measured at each time point; the initial TS content was 19 g/L (dry wt.) for each test and was 16 to 17 g/L by the 24-hr sample.

Conclusion of the Spiked-Batch Tests at 53° C.

Results from the two spiked-batch tests are reported in Tables 19 and 20. It should be kept in mind that the time zero samples represent biosolids that were at a temperature of 53° C. for two to three minutes before the samples could be collected and cooled. Thus, differences between the time zero values for a given organism may reflect differences in the amount of time elapsed before the sample was collected rather than differences in the amount of the organism spiked.

TABLE 19

Results from First Spiked-batch Test

Concentration of Indicated Organism ($\text{Log}_{10}$/g TS) [a]

| Time (hours) | Ascaris ova | | Poliovirus | Coliphage [b] | |
|---|---|---|---|---|---|
| | viable | non-viable | | Somatic | Male-specific |
| 0 | 3.35 | 3.27 | 3.21 | 4.67 | 3.09 |
| 0.17 | 1.97 | 3.60 | <0.40 | ND | ND |
| 0.5 | <0.46 | 3.46 | <0.42 | 3.58 | 2.01 |
| 1 | <0.90 | 3.42 | <0.41 | 3.64 | 1.39 |
| 2 | ND | ND | <0.40 | 3.85 | 0.97 |
| 4 | ND | ND | <0.40 | 3.70 | 0.49 |
| 8 | ND | ND | <0.37 | 3.84 | 0.96 |
| 24 | ND | ND | ND | 3.49 | 0.31 |

[a] Concentrations of poliovirus were measured as pfu and concentrations of coliphage were measured as most-probable-number (MPN). All concentrations were normalized per gram TS (dry weight).
[b] The concentrations of somatic and male-specific coliphages before spiking the reactor were 4.20 and 2.20 $\log_{10}$ MPN/g TS, respectively.
[c] ND, not determined.

TABLE 20

Results from Second Spiked-batch Test [a]

Concentration of Indicated Organism ($\text{Log}_{10}$/g TS)

| Time (hours) | Ascaris ova | | Poliovirus | Coliphage | |
|---|---|---|---|---|---|
| | viable | non-viable | | Somatic | Male-specific |
| 0 | 3.29 | 3.25 | 4.85 | 3.76 | 2.62 |
| 0.17 | 2.19 | 3.49 | 2.02 | ND | ND |
| 0.5 | <0.39 | 3.52 | <0.51 | 3.82 | 2.41 |
| 1 | <0.86 | 3.48 | <0.33 | 3.77 | 0.99 |
| 2 | ND | ND | <0.30 | 3.61 | 1.20 |
| 4 | ND | ND | <0.37 | 3.82 | 0.83 |
| 8 | ND | ND | <0.37 | 3.74 | 0.90 |
| 24 | ND | ND | ND | 3.25 | 0.61 |

[a] Notes are as in Table 19. Concentrations of somatic and male-specific coliphages before spiking were 4.17 and 2.11 $\log_{10}$ MPN/g TS, respectively.

Poliovirus density was reduced by nearly three-logs within 10 minutes in both tests. In the first test, the concentration at 10 minutes was below the method detection limit. Due to a much higher concentration in the time zero sample for the second test, the poliovirus concentration did not decrease to below the detection limit until the 30-minute sample. Overall, however, these data suggest that poliovirus is rapidly inactivated at 53° C.

Figure 9:
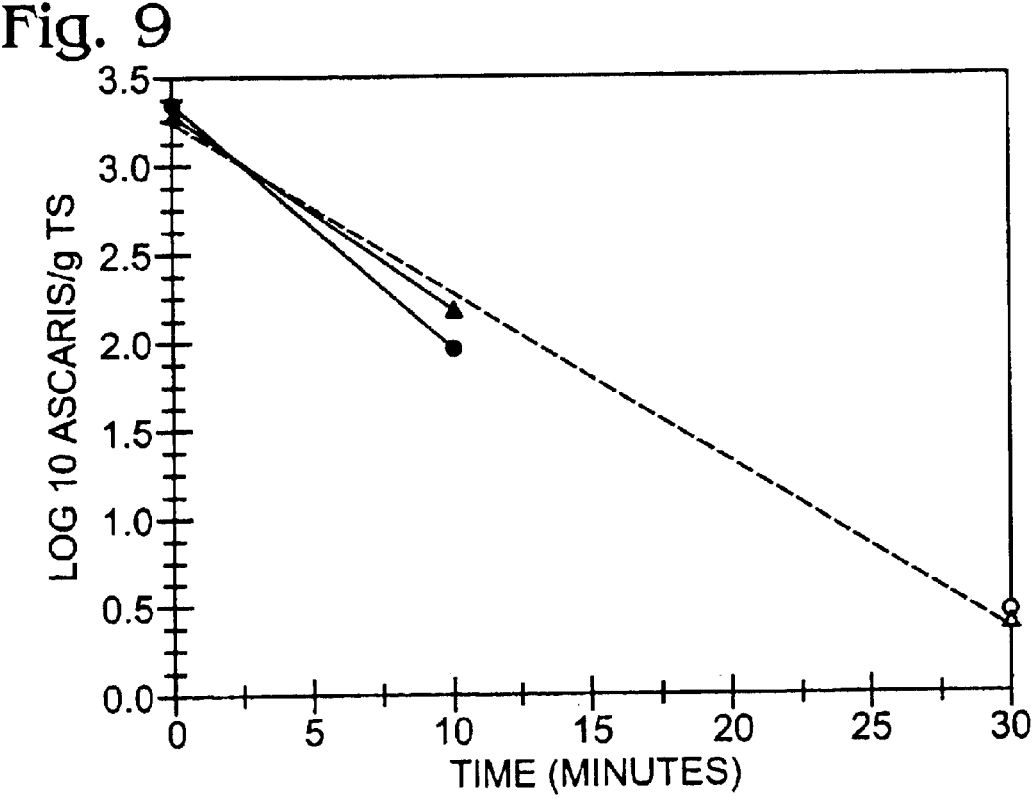
FIG. 9 is a plot of *Ascaris* ova data from 53° C. spiked-batch tests.

Ascaris ova density also declined rapidly, although measurable concentrations were obtained in the time zero and 10-minute samples in both tests, as shown in FIG. 9. FIG. 9 is a plot of Ascaris ova density data from both spiked-batch tests. The open symbols represent values below the detection limit. Lines represent linear fits to the data for either the first two points (solid lines) or all three points (dashed line). The fits to all three points were similar for the two tests, so only one is shown. As with the data that were obtained in one of the spiked-batch tests at 55° C., it is possible to estimate an inactivation rate coefficient by fitting a line between the two positive data points for each of the tests at 53° C. Based on these fits, the average inactivation rate coefficient at 53° C. was 17 $hr^{-1}$ (410 $d^{-1}$). This rate is higher than that estimated for the one spiked-batch test at 55° C. that resulted in measurable Ascaris ova in any of the samples (13 $hr^{-1}$, or 320 $d^{-1}$). However, the Ascaris ova recovered in the time zero samples in the 53° C. spiked-batch tests were one-log higher than in the time zero sample in the 55° C. spiked-batch test. This may indicate significantly greater inactivation during the interval preceding the time zero sample at 55° C. than at 53° C.

FIG. 10 is a plot of male-specific coliphage data from both spiked-batch tests. The somatic coliphage density declined by about one-log within the first 30 minutes in the first test, but there was negligible further decline through 24 hours. In the second test, the somatic coliphages density declined by about one-half log but only after 24 hours of batch treatment. These data are consistent with relatively low reduction of somatic coliphage density across the CFSTR, as described previously herein.

The male-specific coliphage density was reduced by 1.5 logs to 2 logs in the first two hours of the spiked-batch tests at 53° C. It appears, however, that there is a resistant fraction of these coliphages, because there was limited further removal between two hours and 24 hours. These data are consistent with observations made in the other batch tests at both 53° C. and 55° C.

Microbiological Methods

Following is a summary of methods used for the microbiological analyses. Feed samples were obtained in 1 L aliquots and later split into two 500 mL aliquots in the microbiology laboratory, while biosolids samples from the CFSTR or batch tank were collected in two 500 mL aliquots. One 500 ml volume of each sample was blended for the Ascaris ova resident indicators, and Salmonella analyses. The remaining 500 ml volume was unblended for the poliovirus and dry weight determination. Dry weight was determined by heating duplicate 25-mL volumes of the unblended sludge samples in accordance with Standard Method 2540G.

Samples were processed for Ascaris ova analyses using magnesium sulfate flotation (Tulane Method) and microscope examination for survival of the eggs by the demonstration of viable larvae inside the eggs for each sample tested. A total of six slides were examined for viable ova in the feed samples and at least 100 eggs (nonviable) were counted from each biosolids sample (from the CFSTR or the batch tank) for determination of detection limits.

To prepare a spike, poliovirus as infected cell culture lysate was purified by centrifugation-filtration. The sample was concentrated 10-fold (from 10 mL poliovirus lysate to 1 mL) and washed three times in sterile phosphate-buffered saline to remove any potential inhibitory substances. Polioviruses were analyzed by the flocculation and membrane filter elution method as prescribed by the EPA. Poliovirus concentrations were determined by plaque assay using the Buffalo green monkey kidney (BGMK) cell line. Analysis of several samples was repeated using a most-probable-number (MPN) format in an effort to increase the measurable reduction of poliovirus titer. Larger sample volumes were also used to decrease the detection limit.

Resident densities of coliphages (somatic and male-specific) were analyzed by an enrichment method (EPA Method 1601) in an MPN format to compute coliphage titers. Resident densities of *Salmonella* were analyzed by enrichment in buffered peptone water followed by selective enrichment in Rappaport Vassiliadis Broth in an MPN format. Samples were subcultured to *Salmonella-Shigella* agar and colonies suggestive of *Salmonella* were identified biochemically by the rapid NFT identification system.

Resident densities of fecal coliform bacteria were analyzed by a two-step MPN format as described in Standard Methods for the Examination of Water and Wastewater. Resident densities of *Clostridium perfringens* spores were analyzed by a five-tube MPN format assay in iron milk medium after heat-treatment of each sample dilution at 60° C. to 70° C. for 20 minutes.

Thus, a method for the thermophilic treatment of wastewater sludge has been disclosed. It will be appreciated that further variations and modifications thereof may be made within the scope of the invention as defined in the appended claims.

We claim:

1. A method of treating wastewater sludge comprising:
   pumping, continuously, raw sludge into a first digester and treating the raw sludge at a specific temperature of between about 51° C. to 60° C.;
   transferring the treated wastewater sludge to a batch tank;
   treating the wastewater sludge in the batch tank, anaerobically, at a thermophilic temperature which is not more than 2° C. warmer than the specific temperature in the first digester; and
   disposing of the treated wastewater sludge as a Class A biosolid.

2. The method of claim 1 wherein treating the wastewater sludge in the batch tank includes retaining the sludge in the batch tank for a minimum time period of between about 0.5 hours and 5 hours.

3. The method of claim 1 wherein treating the wastewater-sludge in the first digester includes retaining the sludge in the first digester for an average time period of at least four days.

4. The method of claim 1 wherein said disposing includes directing the treated sludge to a third set of digesters, operating at a temperature of about 35° C. for a time period of at least 8 days.

5. The method of claim 1 wherein the method of treating includes treating wastewater sludge to meet EPA VAR standard by a treatment option taken from the group of options consisting of:
   (1) oversizing the first digester to increase an average retention time of the wastewater sludge therein;
   (2) oversizing the batch tank to increase the average retention time of the wastewater sludge therein;
   (3) providing a third digester which includes a thermophilic digester;
   (4) providing a third digester which includes a mesophilic digester wherein sludge leaving the batch tank is cooled to mesophilic temperatures in a range of between about 35° C. to 42° C., and digested further in the mesophilic digester; and
   (5) providing alternative VAR option downstream of the first and second digester taken from the group of alternate VAR options including 40-day additional digestion test; 30-day additional digestion test; subsurface injection of biosolids.

6. The method of claim 1 wherein the batch tank is a plug-flow reactor.

7. A method of treating wastewater sludge comprising:
   pumping, continuously, raw sludge into a first digester and treating the raw sludge at a specific temperature of between about 51° C. to 60° C.;
   transferring the treated wastewater sludge to a plug-flow reactor;
   treating the wastewater sludge in the plug-flow reactor; anaerobically, at a thermophilic temperature which is not more than 2° C. warmer than the specific temperature in the first digester, for a minimum time period of between about 0.5 hours and 5 hours; and
   disposing of the treated wastewater sludge as a Class A biosolid.

8. The method of claim 7 wherein treating the wastewater sludge in the first digester includes retaining the sludge in the first digester for an average time period of at least four days.

9. The method of claim 7 wherein said disposing includes directing the treated sludge to a third set of digesters, operating at a temperature of about 35° C. for a time period of at least 8 days.

10. The method of claim 7 wherein the method of treating includes treating wastewater sludge to meet EPA VAR standard by a treatment option taken from the group of options consisting of:
    (1) oversizing the first digester to increase an average retention time of the wastewater sludge therein;
    (2) oversizing the plug-flow reactor to increase the average retention time of the wastewater sludge therein;
    (3) providing a third digester which includes a thermophilic digester;
    (4) providing a third digester which includes a mesophilic digester wherein sludge leaving the batch tank is cooled to mesophilic temperatures in a range of between about 35° C. to 42° C., and digested further in the mesophilic digester; and
    (5) providing alternative VAR option downstream of the first and second digesters taken from the group of alternate VAR options including 40-day additional digestion test; 30-day additional digestion test; subsurface injection of biosolids.

11. A wastewater sludge treatment system comprising:
    a first thermophilic digester for treating raw wastewater sludge at a specific temperature in a range of between about 51° C. to 60° C., and discharging a treated wastewater sludge;
    a plug-flow reactor for receiving said treated wastewater sludge discharged from said first digester and for thermophilically treating sludge at a temperature in a range of between about 51° C. to 60° C. and not more than 2° C. warmer than said specific temperature in said first digester, for between about 0.5 hours and 5 hours, wherein said plug-flow reactor which includes plural vertically disposed reactor vessels; a sludge feed manifold for transferring sludge from said first thermophilic digester to said reactor vessels; a valved, sludge feed pipe for transferring sludge from said sludge feed manifold to said reactor vessels, wherein said sludge feed pipe directs sludge to the top of said reactor vessels and is configured to direct sludge to the top and sides of the reactor vessels and is sized to maintain solids in suspension; a weir located accent the top of the reactor vessels to remove floatable sludge components and a valved outlet pipe; and a disposal mechanism for disposing of the treated wastewater sludge as a Class A biosolid.

12. The wastewater sludge treatment system of claim 11 wherein said valved outlet pipe is connected to said sludge feed manifold downstream of said sludge feed pipe.

13. The wastewater sludge treatment system of claim 11 wherein said reactor vessel includes a baffle located intermediate the top and bottom thereof.

14. The wastewater sludge treatment system of claim 13 wherein said baffle has a conical configuration, the point thereof being directed upwards in said reactor vessel.

15. The wastewater sludge treatment system of claim 13 wherein said baffle has a truncated conical configuration, the opening thereof being directed upwards in said reactor vessel.

16. The wastewater sludge treatment system of claim 13 wherein each reactor vessel includes plural baffles.

17. The wastewater sludge treatment system of claim 11 wherein said disposal mechanism includes a mesophilic digester for finally treating the sludge prior to disposal thereof.

18. The wastewater sludge treatment system claim 11 is constructed and arranged to EPA VAR standard by a treatment options taken from the group of options consisting of:
(1) oversizing the first digester to increase an average retention time of the wastewater sludge therein;
(2) oversizing the batch tank to increase the average retention time of the wastewater sludge therein;
(3) providing a third digester which includes a thermophilic digester;
(4) providing a third digester which includes a mesophilic digester wherein sludge leaving the batch tank is cooled to mesophilic temperatures in a range of between about 35° C. to 42° C., and digested further in the mesophilic digester; and
(5) providing alternative VAR option downstream of the first and second digester taken from the group of alternate VAR options including 40-day additional digestion test; 30-day additional digestion test; subsurface injection of biosolids.

* * * * *